US 8,177,786 B2

(12) United States Patent
Leyden et al.

(10) Patent No.: US 8,177,786 B2
(45) Date of Patent: May 15, 2012

(54) ORTHOPAEDIC TRAUMA HIP SCREW ASSEMBLY AND ASSOCIATED METHOD

(75) Inventors: Matthew V. Leyden, St. Paul, MN (US); Matthew S. Wallace, Fort Wayne, IN (US); Daniel S. Horwitz, Salt Lake City, UT (US); George J. Haidukewych, Tampa, FL (US); David A. Hawkes, Layton, UT (US); Marc E. Ruhling, Goshen, IN (US)

(73) Assignee: DePuy Products, Inc., Warsaw, IN (US)

( * ) Notice: Subject to any disclaimer, the term of this patent is extended or adjusted under 35 U.S.C. 154(b) by 775 days.

(21) Appl. No.: 11/731,348

(22) Filed: Mar. 30, 2007

(65) Prior Publication Data

US 2008/0255559 A1    Oct. 16, 2008

(51) Int. Cl.
*A61B 17/76*     (2006.01)
(52) U.S. Cl. .......................................................... 606/65
(58) Field of Classification Search ................ 606/62–68
See application file for complete search history.

(56) References Cited

U.S. PATENT DOCUMENTS

| | | | | |
|---|---|---|---|---|
| 2,628,614 A | * | 2/1953 | Briggs | 606/67 |
| 2,672,861 A | * | 3/1954 | Salo et al. | 606/63 |
| 3,029,811 A | | 4/1962 | Yost | |
| 3,374,786 A | | 3/1968 | Callender, Jr. | |
| 4,432,358 A | * | 2/1984 | Fixel | 606/66 |
| 4,438,762 A | | 3/1984 | Kyle | |
| 4,441,492 A | * | 4/1984 | Rydell et al. | 606/67 |
| 4,612,920 A | * | 9/1986 | Lower | 606/66 |
| 4,616,638 A | | 10/1986 | Griggs | |
| 4,621,629 A | | 11/1986 | Koeneman | |
| 4,628,923 A | * | 12/1986 | Medoff | 606/65 |
| 4,657,001 A | * | 4/1987 | Fixel | 606/66 |
| 4,708,132 A | * | 11/1987 | Silvestrini | 606/66 |
| 4,733,654 A | | 3/1988 | Marino | |
| 5,007,910 A | * | 4/1991 | Anapliotis et al. | 606/65 |
| 5,032,125 A | | 7/1991 | Durham et al. | |
| 5,041,116 A | * | 8/1991 | Wilson | 606/65 |

(Continued)

FOREIGN PATENT DOCUMENTS

| | | |
|---|---|---|
| DE | 918531 | 9/1954 |
| EP | 1797835 | 6/2007 |

OTHER PUBLICATIONS

European Search Report of European Application EP 08 25 1214.

*Primary Examiner* — Eduardo C Robert
*Assistant Examiner* — Jerry Cumberledge
(74) *Attorney, Agent, or Firm* — Maginot, Moore & Beck

(57) ABSTRACT

A hip screw assembly for fixation of a fractured femur is provided. The hip screw assembly includes a screw for engagement with the femur. The hip screw assembly also includes a barrel defining a cavity in the barrel. The barrel is fixedly secured to the plate. The screw including a portion thereof fitted in the cavity of the barrel. The hip screw assembly also includes a stop positionable in the barrel. The stop provides a limit on the movement of said screw in said barrel. The screw and the barrel have a first arrangement between each other in which the screw slides in the cavity of said barrel a first selectable predetermined distance and a second arrangement in which the screw slides a second selectable predetermined distance. The second distance is greater than the first distance.

35 Claims, 33 Drawing Sheets

U.S. PATENT DOCUMENTS

| | | | |
|---|---|---|---|
| 5,324,292 A | 6/1994 | Meyers | |
| 5,454,813 A * | 10/1995 | Lawes | 606/62 |
| 6,443,954 B1 * | 9/2002 | Bramlet et al. | 606/62 |
| 6,695,844 B2 * | 2/2004 | Bramlet et al. | 606/66 |
| 7,135,023 B2 * | 11/2006 | Watkins et al. | 606/65 |
| 2001/0000186 A1 * | 4/2001 | Bramlet et al. | 606/66 |
| 2003/0078581 A1 * | 4/2003 | Frei et al. | 606/68 |
| 2005/0107800 A1 * | 5/2005 | Frankel et al. | 606/92 |
| 2005/0149024 A1 * | 7/2005 | Ferrante et al. | 606/62 |
| 2005/0234457 A1 * | 10/2005 | James et al. | 606/69 |
| 2006/0149247 A1 * | 7/2006 | Frigg et al. | 606/64 |
| 2006/0241604 A1 * | 10/2006 | Frigg et al. | 606/62 |
| 2006/0241606 A1 * | 10/2006 | Vachtenberg et al. | 606/65 |
| 2007/0270847 A1 * | 11/2007 | Shaw | 606/65 |

* cited by examiner

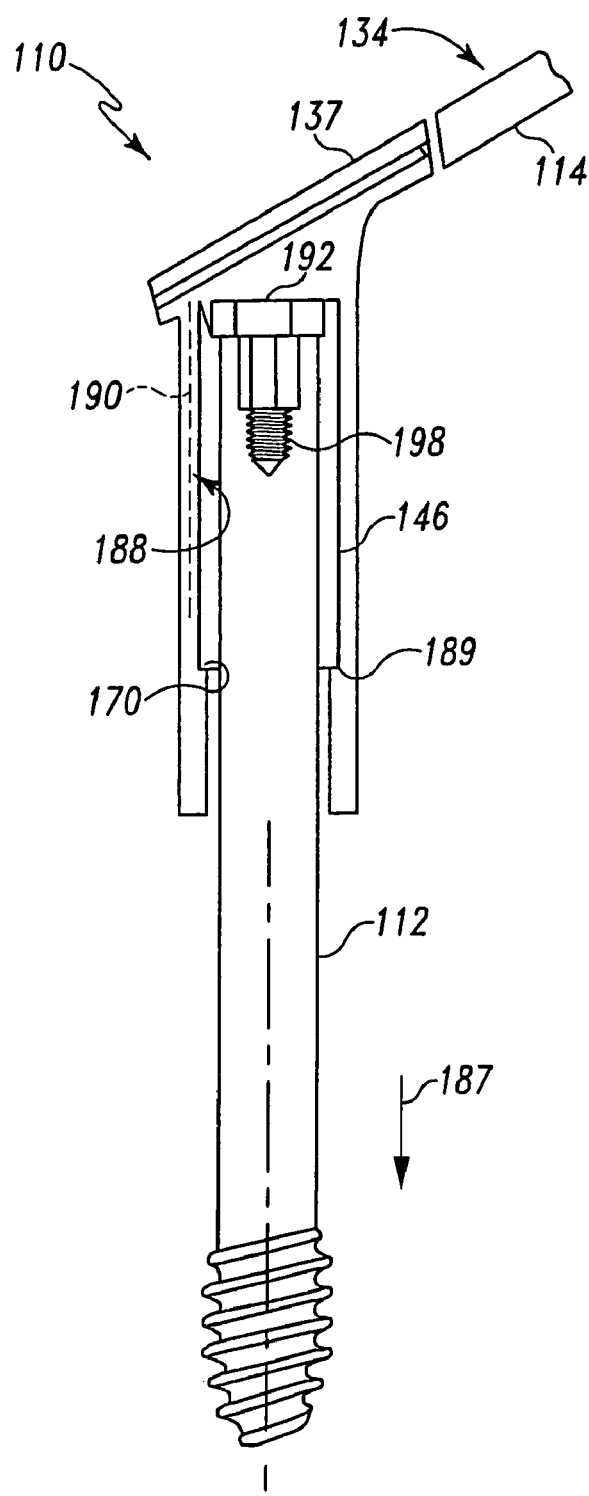
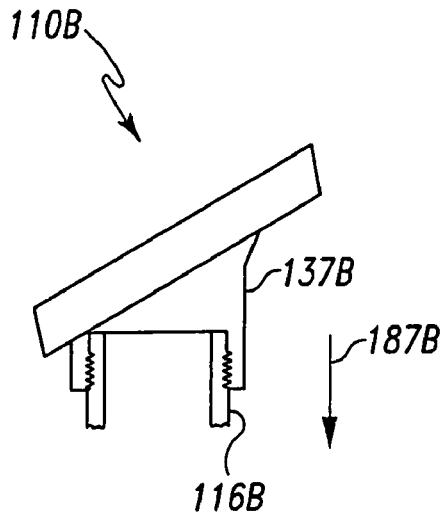
Fig. 24A
Fig. 24B
Fig. 24

ORTHOPAEDIC TRAUMA HIP SCREW ASSEMBLY AND ASSOCIATED METHOD

FIELD

This application relates generally to the field of orthopedics, and more specifically to appliances used in the reduction of hip fractures in which the neck of the femur is the site of the fracture.

BACKGROUND

Hip fractures, wherein the femur is fractured one or more times in the area of the femur or immediately adjacent the head are comparatively common. A great many devices have been proposed for the reduction of fractures of this type. While many of these devices have found the application and have advantages relative one to another, there remain some problems and areas of continuing concern.

Such reduction devices consist, basically, of an elongate lag screw which is threaded on one end to be threadably received in the head of the femur, and is secured to a plate such that when the lag screw is tightened, the head of the femur is forcibly compressed at the fracture line to the remainder of the femur.

It has also been recognized that various adjustment features are important in treating certain femoral fractures. In general, fastener devices with such adjustment features employ a guide sleeve which is imbedded in one bone segment, such as the upper segment of the femur, in order to receive and adjustably hold one end of an axially elongated shaft, e.g. a lag screw, which extends through both fractured bone segments, with the end of the shaft opposite the guide sleeve being provided with structure for securing the shaft to the head of the femur. Because of absorption occurring during the healing process, it has been necessary, in some instances, to accommodate a certain amount of telescoping movement between the shaft and the guide sleeve.

Functionally, some of these devices perform quite satisfactorily for many fractures of the femur but are extremely difficult for the surgeon to properly implant. It is, therefore, of great importance to provide a fixation device which is not only functional in providing the necessary stability and guidance in the reduction of the fracture, but can be efficiently, accurately and quickly implanted by the surgeon.

A compression hip screw assembly is used to apply compression across a proximal femoral fracture. The assembly includes a lag screw, a barrel, a plate and cortical screws to attach the plate to bone. A compression hip screw may be used to allow for sliding compression of the lag screw so that the fracture could be adequately reduced under normal weight bearing. The applying of force to the fracture site promotes healing. This phenomenon is known as Wolff's law. By providing a load to the fracture site atrophy of the fracture site can be avoided.

When load is applied to a compression hip screw, the screw which has a tendency to back out laterally through the plate or to cut out medially through the head of the femur.

When the screw threads tend to advance medially, such phenomenon is known as cutout. The screw tends to advance medially and may cause problems to the compression of the fracture site and may move medially to the point of having the screw leave the bone or femur.

Alternatively the screw threads of the hip screw during compression may back out or move away from the head of the femur in a lateral direction.

Such movement of the threads of the lag screw may cause the lag screw to move against the plate and eventually to have a portion of the lag screw extend past the plate and cause soft tissue irritation and other difficulties to the patient.

A compression hip screw is used to allow for sliding compression of the lag screw so that the fracture can be adequately reduced under normal weight bearing. In prior art lag screws the lag screws may often compress too far and laterally back out of the barrel creating soft tissue irritation and femoral head collapse. In some indications, the surgeon may prefer the lag screw be fixed with respect to the barrel so that it is not able to provide sliding compression. For example, in a subtrochanteric fracture or reverse oblique fracture, the surgeon would prefer the lag screw and barrel to be rigid. The surgeon must choose between having a compression hip screw or a fixed hip screw in the surgery room, or the surgeon may require that both be present.

To assist in preventing cutout, while providing compression, the screw may be permitted to slide along the barrel but not rotate in the barrel. Such configurations have been provided that provide for anti-rotation features positioned between the barrel and the screw. Some devices require different lag screws or barrels to be inserted depending on the surgeon's requirements to limit compression, rotation, or both. For example, a separate lag screw or barrel may be required to prevent rotation by requiring the keying of the barrel to the screw.

Other attempts to provide for keying or preventing rotation between the screw and the barrel include the use of clips, locking pins, ribs or tabs. These configurations require the use of complex insertion and removable tools, odd cross-sectional designs, and may increase the amount of lag screw and barrel inventory required by the medical facility.

SUMMARY

An aspect of the present invention provides for selectable use of compression, no compression or varying amounts of compression. An aspect of the present invention further permits the choosing of keying or non-keying between the barrel and the compression screw to permit rotation between the screw in the barrel or to prevent rotation of the screw with respect to the barrel.

An aspect of the present invention allows the surgeon to utilize the same lag screw and barrel regardless of the keying decision. If the surgeon chooses to key the lag screw, he inserts the key in key screw into the lateral end of the lag screw. This device provides a simple, intuitive method of keying the lag screw as well as provides a simple means of removing the screw, if necessary.

An aspect of the present invention utilizes two small components, a key and a key screw to engage the lateral end of the lag screw and to engage the sleeve to provide rotational control. The sleeve has longitudinally extending protrusions that mate with the longitudinally extending grooves in the barrel. The sleeve is snapped, during the manufacturing process, onto the lag screw to allow for it to be free to rotate inside the barrel.

The key has two corresponding hexagonal geometries, one that mates with the hexagonal shape in the lag screw and another that mates with a hexagonal in the sleeve to secure the lag screw and the sleeve together. The key screw has threads that mate with the internal threads of the lag screw.

When fully assembled, the lag screw is prevented to actually rotate with respect to the barrel. A lag screw is used in conjunction with a side plate and barrel. The lag screw is able to slideably compress within the barrel.

An aspect of the present invention may include a barrel with an elongated hole with grooves to receive the lag screw and threads to receive the controlled collapse cap. The controlled collapse cap is included to optionally allow for controlled compression of the lag screw.

In the treatment of proximal femoral fractures, it is common to utilize various compression hip screw devices. A lag screw is used in conjunction with a side plate and barrel. The lag screw is able to slideably compress within the barrel. The present invention allows for a threaded cap to be inserted into the threads in the barrel to provide control collapse of the lag screw.

The barrel may have threads in the lateral end that are used to receive the controlled collapse cap. The controlled collapse cap can be available in multiple lengths so that the surgeon can interoperatively select the appropriate length. In this way, the surgeon can select the amount of sliding compression that is desired by the lag screw. The medial end of the control collapse cap may provide a stop against the lateral end of the sleeve.

According to an embodiment of the present invention, a hip screw assembly for fixation of a fractured femur is provided. The hip screw assembly includes a screw for engagement with the femur. The hip screw assembly also includes a barrel defining a cavity in the barrel. The barrel is secured to the plate. The screw includes a portion fitted in the cavity of the barrel. The hip screw assembly also includes a stop positionable in the barrel. The stop provides a limit on the movement of said screw in said barrel. The screw and the barrel have a first arrangement between each other in which the screw slides in the cavity of said barrel a first selectable predetermined distance and a second arrangement in which the screw slides a second selectable predetermined distance. The second distance is greater than the first distance.

The compression screw of the present invention may be utilized for all sub-trochanteric fractures, intra-capsular fractures when anti-rotation option is employed, and sub-trochanteric fractures. Comminuted fractures of the greater trochanter, reverse oblique fractures, and high sub-trochanteric fractures may also be treated using the trochanteric plate option of the compression hip screw of an embodiment of the present invention. The comminuted fractures, reverse oblique fractures and high sub-trochanteric fractures require the use of a sub-trochanteric plate to prevent medialization of the femoral shaft.

The compression hip screw of an embodiment of the present invention may use a lag screw first technique in which the screw is first inserted into the femur and once in position the plate is connected to the screw and secured to bone. It should be appreciated that the anti-rotation feature and selectable compression feature of an embodiment of the present invention may be utilized in a compression hip screw in which is either a lag screw first device or a utilizes a plate first technique.

When assembling the compression hip screw of an embodiment of the present invention, the lag screw may be inserted through the barrel and the sleeve is pressed onto the end of the lag screw. The lag screw/sleeve connection is intended to prevent the lag screw from disengaging from the barrel in the medial direction. The lag screw of an aspect of the present invention may include a truncated unilateral thread profile that may increase the force required to induce pull-out of the lag screw. The truncated unilateral thread profile may also reduce the stress applied to the femoral head that may lead to cutout.

The present invention may further include a collapse cap that can be threaded into the lateral side of the barrel to limit the collapse of the lag screw and prevent the lag screw from laterally protruding from the barrel. The collapse cap can come in a variety of lengths such that the compression amount may be varied depending on the choice of the collapse cap.

According to one aspect of the hip screw assembly, the assembly also includes a stop positionable in the barrel. The stop provides a limit on the movement of the screw in the barrel.

According to another aspect of the hip screw assembly, the hip screw assembly further includes a second stop positionable in the barrel. The second stop provides a limit on the movement of the screw in the barrel. The second stop defines a second stop length.

According to another aspect of the hip screw assembly, the first stop defines a first stop length. The second stop length and the first stop length are different from each other.

According to another aspect of the hip screw assembly, the stop threadably engages the barrel.

According to another aspect of the hip screw assembly, the hip screw assembly further includes a set screw to lock the stop in a fixed position.

According to another aspect of the hip screw assembly, the hip screw assembly further includes a sleeve positioned between the barrel and the screw.

According to another aspect of the hip screw assembly, the hip screw assembly further includes a key for angularly orienting the screw with respect to the sleeve.

According to another aspect of the hip screw assembly, the hip screw assembly further includes a sleeve positioned between the barrel and the screw, and a key for angularly orienting the screw with respect to the sleeve. The sleeve defines an angular orientation feature on the sleeve and the barrel defines an angular orientation feature on the barrel. The angular orientation feature on the sleeve cooperates with the angular orientation feature on the barrel for angularly orienting the sleeve to the barrel.

According to another aspect of the hip screw assembly, the key defines first and second spaced apart key flats. The first flat on the key cooperates with a first flat on the screw for angularly locking the key to the screw. The second flat on the key cooperates with a first flat on the sleeve for angularly locking the key to the sleeve.

According to another embodiment of the present invention, a hip screw assembly for fixation of a fractured femur is provided. The assembly includes a screw for engagement with the femur. The screw defines a screw longitudinal centerline.

The assembly also includes a plate for engagement with the femur and a barrel defining a cavity of the barrel. The barrel is secured to the plate. The screw includes a portion of the screw fitted in the cavity of the barrel. The assembly also includes a key for selectively angularly orienting the screw with respect to the barrel in one of a plurality of positions.

According to another aspect of the hip screw assembly, the screw and the barrel define a first arrangement in which the screw is slides in the cavity of the barrel a first distance and a second arrangement in which the screw is slides in the cavity of the barrel a second distance, the second distance being greater than the first distance.

According to another aspect of the hip screw assembly, the hip screw assembly further includes a stop positionable in the barrel. The stop provides a limit on the movement of the screw in the barrel.

According to another aspect of the hip screw assembly, the hip screw assembly further includes a sleeve positioned between the barrel and the screw.

According to another aspect of the hip screw assembly, the hip screw assembly further includes a key for angularly orienting the screw with respect to the barrel.

According to another aspect of the hip screw assembly, the hip screw assembly further includes a sleeve positioned between the barrel and the screw and a key for angularly orienting the screw with respect to the sleeve. The sleeve defines an angular orientation feature on the sleeve and the barrel defines an angular orientation feature on the barrel. The angular orientation feature on the sleeve cooperates with the angular orientation feature on the barrel for angularly orienting the sleeve to the barrel.

According to another aspect of the hip screw assembly, the key defines first and second spaced apart key flats. The first flat on the key cooperates with a first flat on the screw for angularly locking the key to the screw. The second flat on the key cooperates with a first flat on the sleeve for angularly locking the key to the sleeve.

According to another aspect of the hip screw assembly, the first and second spaced apart key flats include a polygon pattern of equally spaced flats.

According to another aspect of the hip screw assembly, the first and second spaced apart key flats include a hexagonal pattern.

According to another aspect of the hip screw assembly, the hip screw assembly further includes a fastener for securing the key to one the sleeve and the screw.

According to another aspect of the hip screw assembly, the angular orientation feature on the sleeve includes a longitudinal protrusion and the angular orientation feature on the barrel includes a longitudinal groove.

According to another aspect of the hip screw assembly, the key is adapted for selectively angularly orienting the screw with respect to the barrel in one of a plurality of positions.

According to another aspect of the hip screw assembly, the hip screw assembly defines a first arrangement including the key and a second arrangement not including the key.

According to yet another embodiment of the present invention, a hip screw assembly for fixation of a fractured femur is provided. The hip screw assembly includes a screw for engagement with the femur. The screw defines a screw longitudinal centerline of the screw. The hip screw assembly also includes a plate for engagement with the femur and a barrel defining a cavity in the barrel. The barrel is secured to the plate. The hip screw assembly also includes a sleeve defining an opening through the sleeve. The sleeve is positioned at least partially in the cavity of the barrel. The hip screw assembly also includes a screw for engagement with the femur. The screw includes a portion of the screw fitted in the opening of the sleeve and a key for selectively angularly orienting the screw with respect to the sleeve in one of a plurality of positions, According to another aspect of the hip screw assembly, the screw and the barrel define a first arrangement between each other in which the screw is slides in the cavity of the barrel a first distance and a second arrangement in which the screw slides in the cavity of the barrel a second distance. The second distance is greater than the first distance.

According to another aspect of the hip screw assembly, the hip screw assembly further includes a stop positionable in the barrel. The stop provides a limit on the sliding of the screw in the barrel.

According to another aspect of the hip screw assembly, the hip screw assembly further includes a second stop positionable in the barrel. The second stop provides a limit on the movement of said screw in the barrel. The second stop defines a second stop length. The first stop defines a first stop length. The second stop length and the first stop length are different from each other.

According to another aspect of the hip screw assembly, the sleeve defines an angular orientation feature on the sleeve and the barrel defines an angular orientation feature on the barrel. The angular orientation feature on the sleeve cooperates with the angular orientation feature on the barrel for angularly orienting the sleeve to the barrel.

According to another aspect of the hip screw assembly, the key defines first and second spaced apart key flats. The first flat on the key cooperates with a first flat on the screw for angularly locking the key to the screw. The second flat on the key cooperates with a first flat on the sleeve for angularly locking the key to the sleeve.

According to another aspect of the hip screw assembly, the first and second spaced apart key flats include a polygon pattern of equally spaced flats.

According to another aspect of the hip screw assembly, the first and second spaced apart key flats include a hexagonal pattern.

According to another aspect of the hip screw assembly, the hip screw assembly further includes a fastener for securing the key to the sleeve or the screw.

According to another aspect of the hip screw assembly, the fastener includes a fastener key interlock feature and the key includes a key fastener interlock feature. The fastener key interlock feature of the fastener and the key fastener interlock feature of the key cooperate to interconnect the fastener to the key.

According to another aspect of the hip screw assembly, the angular orientation feature on the sleeve includes a longitudinal protrusion and the angular orientation feature on the barrel includes a longitudinal groove.

According to another aspect of the hip screw assembly, the key is adapted for selectively angularly orienting the screw with respect to the barrel in one of a plurality of positions.

According to another aspect of the hip screw assembly, the hip screw assembly defines a first arrangement including the key and a second arrangement not including the key.

According to yet another embodiment of the present invention, a method for performing trauma surgery is provided. The method includes the steps of providing a hip screw assembly with a screw, a sleeve, a barrel, a plate, and a keying device, preparing an opening in a bone to receive the screw, determining whether to utilize the keying device depending on patient specific information, and implanting the hip screw assembly onto the bone with one of with the keying device and without the keying device based on the determining step.

According to yet another embodiment of the present invention, another method for performing trauma surgery is provided. The method includes the steps of providing a hip screw assembly with a screw, a sleeve, a barrel, a plate, and a sliding compression limiting device, preparing an opening in a bone to receive the screw, determining whether to provide sliding compression in the hip screw assembly depending on patient specific information, and implanting the hip screw assembly onto the bone with one of with the sliding compression limiting device and without the sliding compression limiting device based on the determining step.

According to another aspect of the method for performing trauma surgery, the providing a hip screw assembly step includes providing the sliding compression limiting device comprises providing the sliding compression limiting device with a plurality of compression length settings, the determining step includes determining the compression length setting desired if any sliding compression should be allowed with the hip screw assembly depending on patient specific information, and the implanting the hip screw assembly step includes implanting the hip screw assembly with the desired compression length setting if any sliding compression should be allowed based on the determining step.

According to another aspect of the method for performing trauma surgery, the sliding compression limiting device provides lateral backout prevention, the determining step includes determining whether lateral backout should be prevented with the hip screw assembly depending on patient specific information, and the implanting the hip screw assembly step includes implanting the hip screw assembly with the sliding compression limiting device if any lateral backout should be prevented based on the determining step.

According to another aspect of the method for performing trauma surgery, the method also includes step of measuring the available sliding distance of the screw in the barrel after screw insertion and the step of providing a plurality of stops. The stops have one of a plurality of lengths and are positionable in the barrel. The implanting the hip screw assembly step includes implanting the hip screw assembly with a selected one of the plurality of stops to provide a sliding distance for the hips screw assembly based on the measured available sliding distance of the screw in the barrel.

The technical advantages of the present invention include the ability to provide a lag screw with rotational control. For example, according to one aspect of the present invention, a hip screw assembly for fixation of a fractured femur is provided. The screw assembly includes a screw for engagement with the femur. The screw defines a screw longitudinal center line. The screw assembly further includes a plate for engaging with the femur and a barrel defining a cavity. The barrel is secured to the plate. The screw includes a portion fitted into the cavity of the barrel. The screw assembly further includes a key for a selectively orienting the screw with respect to the barrel in one of a plurality of positions. Thus the present invention provides the ability to provide lag screw rotational control.

The technical advantages of the present invention further include the ability to provide interoperative choices of keyed and keyless operation. For example, according to another aspect of the present invention a method for performing trauma surgery is provided. The method includes the steps of preparing an opening in a bone to receive a screw. The method further includes the step of providing a hip screw assembly with a sleeve, a barrel, a plate and a keying device. The method further includes the steps of determining whether to utilize the keying device depending on the patient's specific information and implanting the hip screw assembly onto the bone of one of, with the keying device, and without the keying device, based upon the determining step. Thus, the present invention provides the ability to provide interoperative choices of keyed and keyless operation.

The technical advantages of the present invention further include the ability to utilize low inventory by utilizing the same lag screw and barrel for configurations of the compression hip screw both with and without rotational control. For example, according to another aspect of the present invention, a hip screw assembly for fixation of a fractured femur is provided. The hip screw assembly includes a screw for engaging with the femur. The screw defines a screw longitudinal center line. The hip screw assembly further includes a plate for engaging with the femur and a barrel defining a cavity in the barrel secured to the plate. The screw includes a portion fitted into the cavity of the barrel and an optional key for selectively angularly orienting the screw with respect to the barrel in one of a plurality of positions. The hip screw assembly further includes as fastener for securing the optional key to one of the sleeve and the screw. Thus, the present invention provides for low inventory by utilizing the same lag screw and barrel for configurations with and without rotational control.

The technical advantages of the present invention further include the ability to interoperatively limit the amount of sliding compression. For example, according to another aspect of the present invention, a method for performing trauma surgery is provided. The method includes the steps of preparing an opening in the bone to receive a screw and providing a hip screw assembly with a sleeve, a barrel, a plate and a sliding compression limiting device. The method further includes the steps of determining whether to provide sliding compression in the hip screw assembly depending on patient's specific information and implanting the hip screw assembly into the bone with the sliding compression limiting device and without the sliding compression limiting device based on the determining step. Thus the present invention provides the ability to interoperatively limit the amount of sliding compression.

The technical advantages of the present invention further include the ability to interoperatively prevent sliding compression of the compression hip screw. For example, according to another aspect of the present invention, a method for performing trauma surgery is provided including the steps of preparing an opening in a bone to receive a screw. The method further includes the step of providing a hip screw assembly with a barrel, a sleeve, a plate and a sliding compression limiting device. The method further includes the step of determining whether to provide sliding compression in the hip screw assembly depending on patient's specific information. The method further includes the step of implanting the hip screw assembly onto the bone with one of the sliding compression limiting device and without the sliding compression limiting device based on the determining step. Thus the present invention provides for interoperatively preventing sliding compression of the compression hip screw.

The technical advantages of present invention further include the ability to interoperatively prevent lateral backout of the lag screw. For example, according to another of the present invention a method of providing trauma surgery is provided. The method includes the steps of preparing an opening in a bone to receive a screw and providing a hip screw assembly with a sleeve, a barrel, a plate and a sliding compressing limiting device. The sliding compression limiting device prevents lateral backout. Thus the present invention provides the ability to interoperatively prevent lateral backout of a lag screw.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 24 is a plan view, partially in cross-section, of another embodiment of a hip screw assembly according to another embodiment of the present invention showing a screw with a selectable anti-rotation feature;

FIG. 24A is a partial plan view, partially in cross-section, showing a barrel with a shoulder for stopping the upward motion of the sleeve according to yet another embodiment of the present invention;

FIG. 24B is a partial plan view, partially in cross-section, showing a two piece barrel with a shoulder for stopping the downward motion of the sleeve according to another embodiment of the present invention;

Corresponding reference characters indicate corresponding parts throughout the several views. Like reference characters tend to indicate like parts throughout the several views.

DETAILED DESCRIPTION OF THE PREFERRED EMBODIMENTS

Embodiments of the present invention and the advantages thereof are best understood by referring to the following descriptions and drawings, wherein like numerals are used for like and corresponding parts of the drawings.

Figure 1:
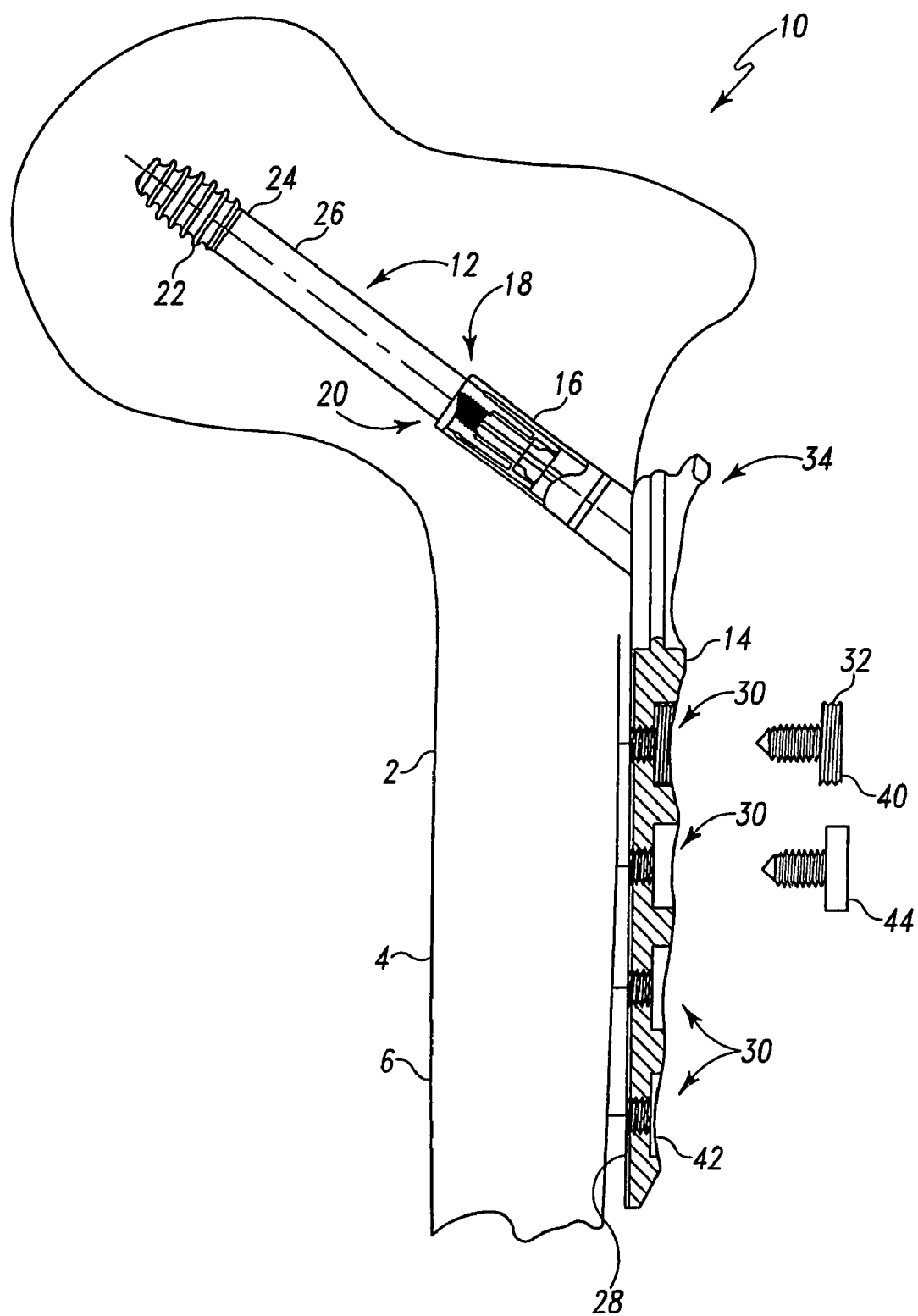
FIG. 1 is a plan view, partially in cross section, of a hip screw assembly according to an embodiment of the present invention.

According to the present invention and referring now to FIG. 1, a hip screw assembly 10 is shown. The hip screw assembly 10 is utilized for fixation of a fractured femur 2. The screw assembly 10 includes a screw 12 for engagement with the femur 2. The hip screw assembly 10 further includes a plate 14 for engagement with the femur 2. The hip screw assembly 10 further includes a barrel 16. The barrel 16 defines a cavity 18 in the barrel 16. The barrel 16 is secured to the plate 14. The screw 12 includes a portion 20 of the screw 12 which is fitted in the cavity 18 of the barrel 16.

The screw 12 may be any suitable compression hip screw which has a portion that may slidingly fit in, for example, barrel 16. The screw 12 includes threads 22 which extend from end 24 of shank 26 of the screw 12. The screw 12 may be made of any suitable durable material and may be made, for example, from a material compatible with the human anatomy, for example, a metal, such as a cobalt chromium alloy, a stainless steel alloy, or a titanium alloy.

The plate 14 may be any plate suitable for contact with other periphery 4 of shaft portion 6 of femur 2. The plate 14 may include a bone contact surface 28 which engages the periphery 4 of the shaft 6 of the femur 2. As shown in FIG. 1 the contact surface 18 may be concave to closely conform to the convex periphery 4 of the shaft 6 of the femur 2. The plate 14 may include a transverse opening 30 or may as shown in FIG. 1, include a plurality of spaced apart transverse openings 30. The openings 30 may each be adapted to receive a screw 32 for cooperation with the femur 2.

The plate 14 may be made of any suitable durable material and may be made of, for example, a titanium alloy, a stainless steel alloy, or a cobalt chromium alloy. For simplicity and to avoid material interactions, the plate 14, barrel 16, and screw 12 may be made of the same material.

Figure 2:
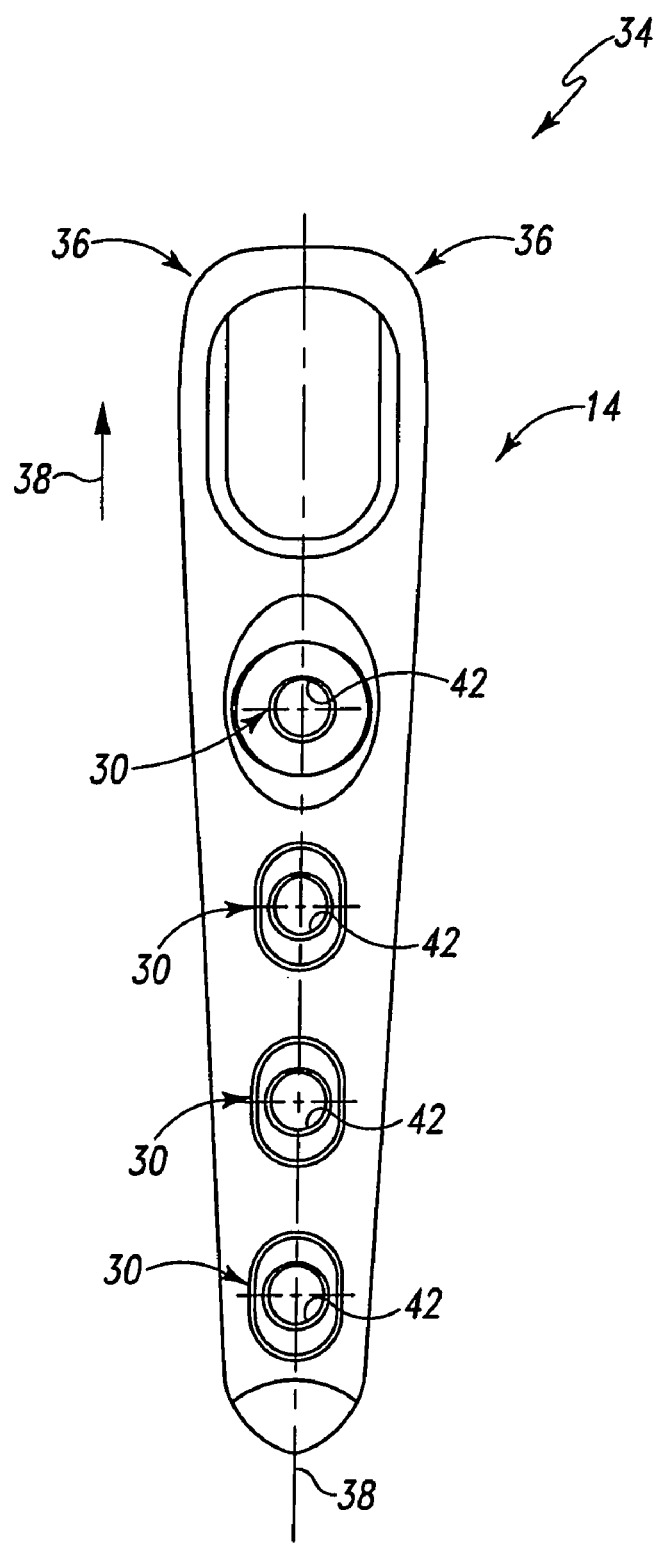
FIG. 2 is a plan view of the plate of the hip screw assembly of FIG. 1.

Referring now to FIG. 2, the plate 14 is shown in greater detail. The plate 14 includes the series of spaced apart openings 30 for receiving the screws 32.

Referring again to FIG. 1, it should be appreciated that the barrel 16 may be secured to the plate 14 in any suitable fashion. For example, the barrel and the plate may be welded, connected by fasteners, such as screws, or may be interferencely fitted to each other. It should likewise be appreciated that the barrel and plate may be integral to each other.

As shown in FIG. 1, the barrel 16 is secured to the plate 14 by means of a barrel plate connector 34. Referring now to FIG. 2, the barrel plate connector 34 may include a channel 36 extending longitudinally along a line parallel to longitudinal center line 38 of the plate 14. The channel 36 may be in the form of two parallel spaced apart channels 36. The channels 36 may cooperate with a mating feature on the barrel 16 to form barrel plate connector 34.

The barrel plate connector 34, as shown in FIG. 32, may be well suited for assembling the plate 14 in the direction of arrow 38. By utilizing the barrel plate connector 34 of FIG. 32, the screw 12 may be first inserted into the femur 2. The barrel 16 may then be placed in the femur 2 in cooperation with the screw 12. Then, by utilizing the barrel plate connection 34, the plate 14 may be connected to the barrel 16 by advancing the plate 14 in the direction of the arrow 38.

The screws 32 for use with the plate 14 may be cortical screws or cancellous screws. The screws 32 may be loosely fitted to the openings 30 or, as shown in FIGS. 1 and 2, the screws 32 may include external threads 40 which mate with internal tapered threads 42 formed in the plate 14. The use of the tapered threads 42 provide for a rigid construct between the screws 32 and the plate 14. It should be appreciated that smaller screws 44 may be slidingly fitted into the openings 30 whereby the screws 44 may provide compression of the plate 14 against the femur 2.

Figure 3:
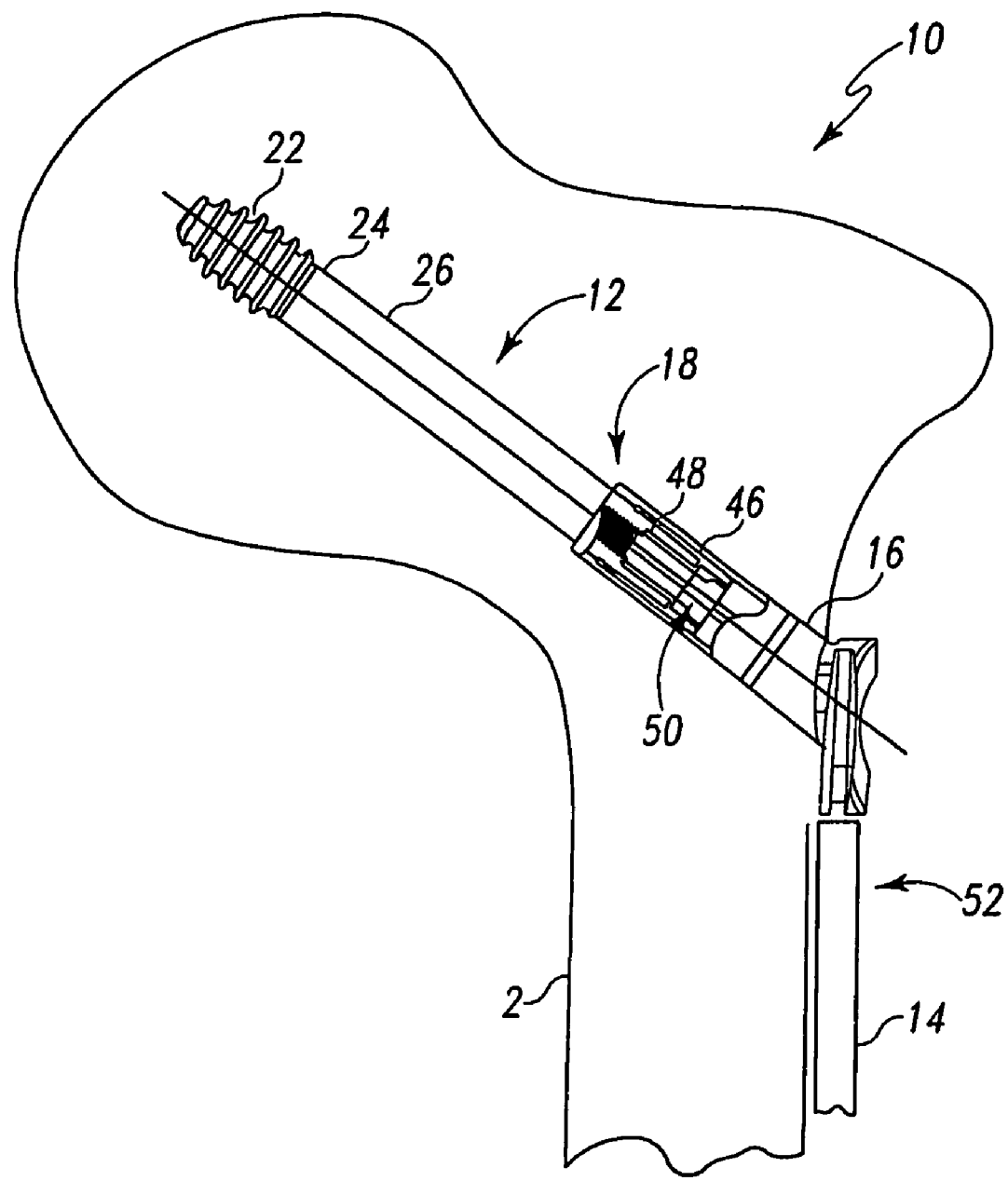
FIG. 3 is a plan view, partially in cross section, of the screw and barrel of the hip screw assembly of FIG. 1.
Figure 4:
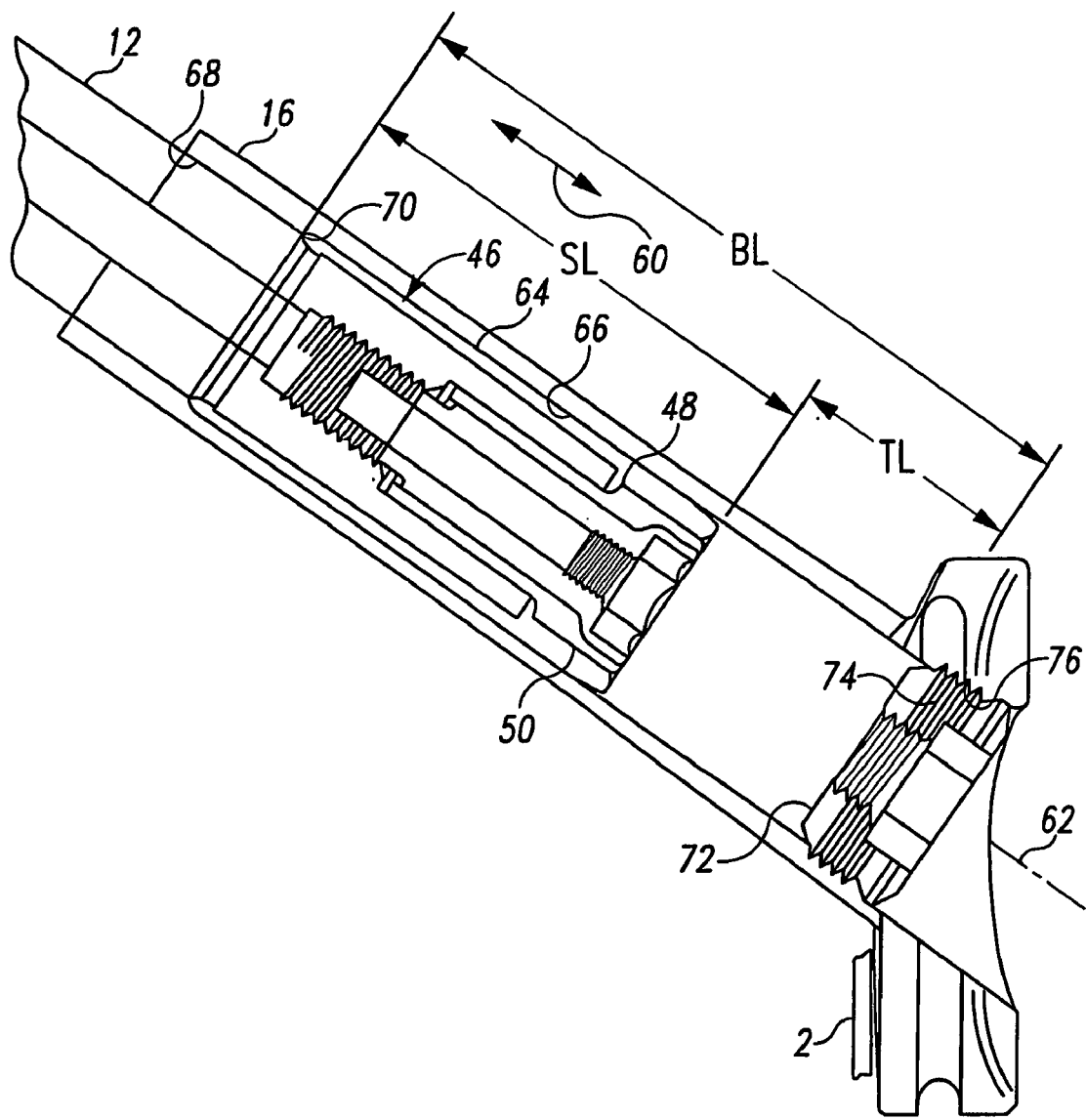
FIG. 4 is an enlarged partial plan view, partially in cross section, of the screw and barrel of the hip screw assembly of FIG. 1.

Referring now to FIGS. 3 and 4 the hip screw assembly 10 is shown in greater detail. The hip screw assembly 10 includes the screw 12 which is fitted at least partially in cavity 18 of barrel 16. It should be appreciated that the screw assembly 10 may include merely the plate 14, the barrel 16, and the screw 12. However, the hip screw assembly 10 may include additional components to provide additional features to the hip screw assembly of the present invention. For example, the hip screw assembly 10 may further include a sleeve for example sleeve 46. The sleeve 46 may be positioned as shown in FIGS. 3 and 4 between the barrel 16 and the shank 26 of the screw 12.

The hip screw assembly 10 may, as shown in FIGS. 3 and 4, further include a key, for example key 48, for providing angular orientation between the screw 12 and the barrel 16. The key 48 may be secured to the screw 12 by, for example, key screw 50.

The barrel 16 may include a channel 52 which mates with plate channel 36 formed on plate 14 (see FIGS. 1 and 2).

Figure 4A:
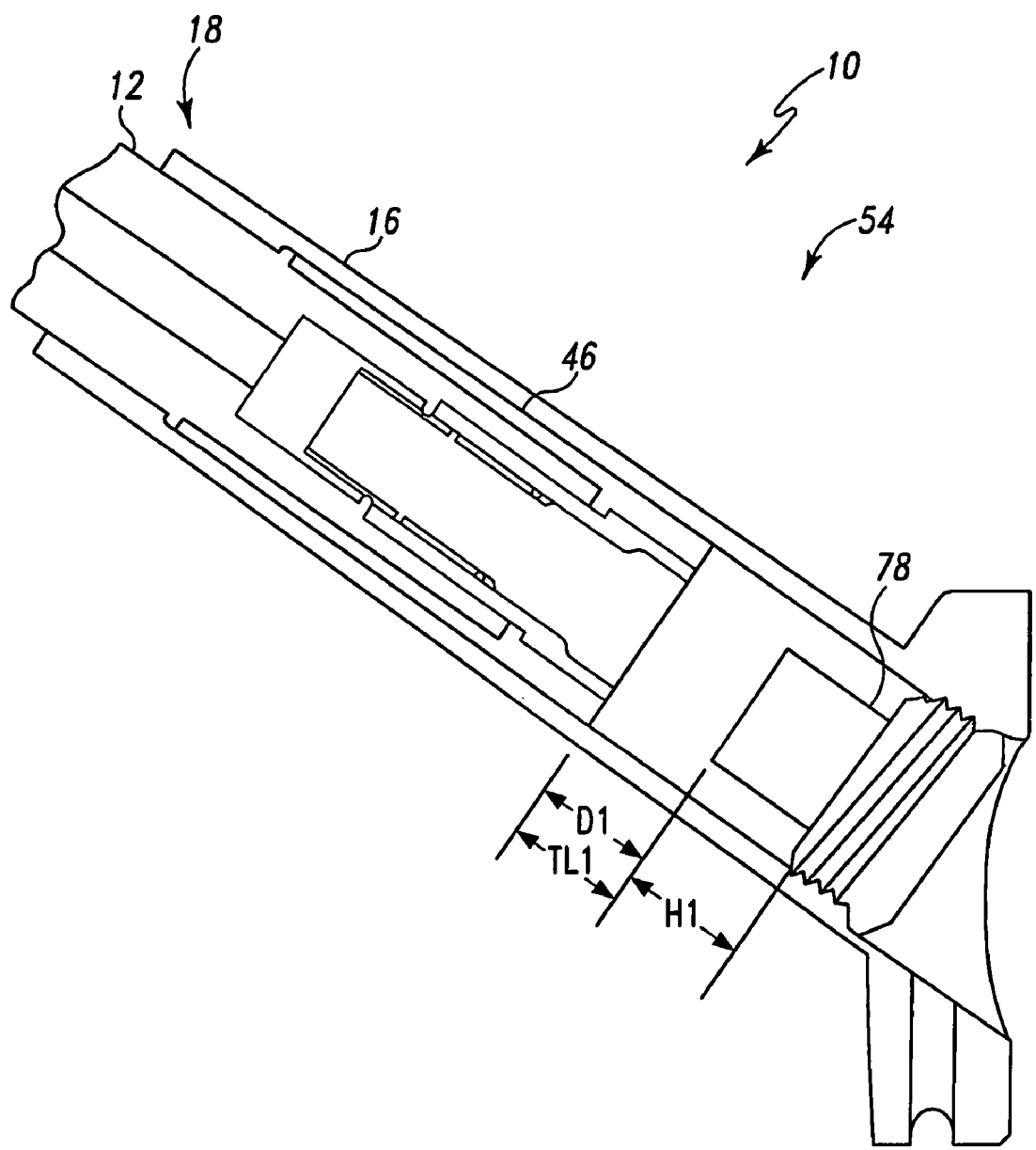
FIG. 4A is a enlarged partial plan view, partially in cross section, of the screw and barrel of the hip screw assembly of FIG. 1 without the key and key screw and including the cap of FIG. 21.
Figure 4B:
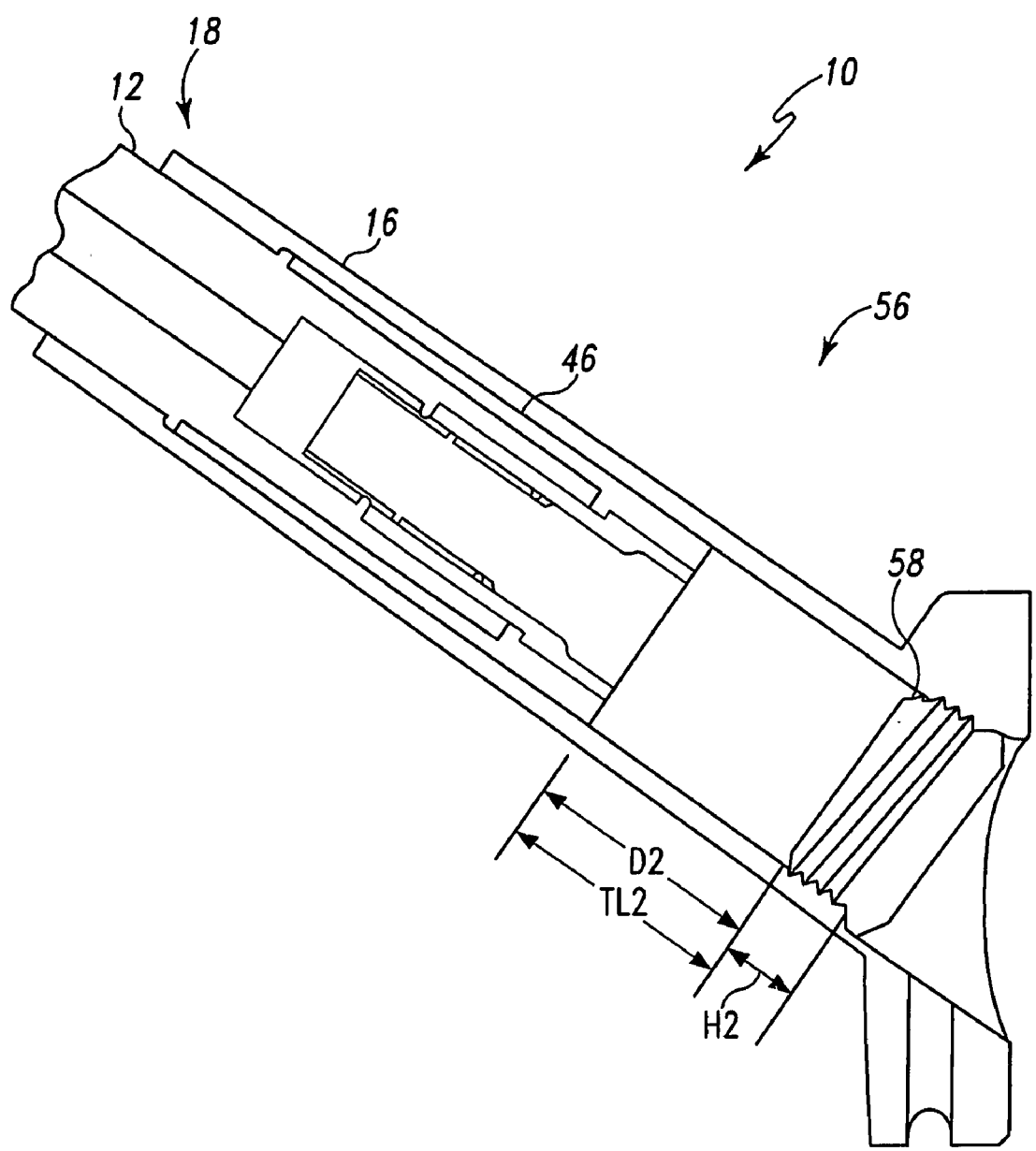
FIG. 4B is a enlarged partial plan view, partially in cross section, of the screw and barrel of the hip screw assembly of FIG. 1 without the key and key screw and including the cap of FIGS. 19-20.

Referring now to FIGS. 4A and 4B, the hip screw assembly 10 of the present invention includes the hip screw 12 and the barrel 16. As shown in FIG. 4A, the screw 12 and the barrel 16 define a first arrangement 54 between the screw 12 and the barrel 16. In the first arrangement 54, the screw 12 is slidingly moveable in the cavity 18 of the barrel 16 a first distance D1.

Referring now to FIG. 4B, the screw 12 and the barrel 16 define a second arrangement 56 between the screw 12 and the barrel 16 in which the screw 12 is slidingly moveable in the cavity 18 of the barrel 16 a second distance D2. As shown in FIGS. 4A and 4B the second distance D2 is greater than the first distance D1. The ability to provide varied travel length distances, such as D1 or D2, or varying amounts of sliding movement of the screw 12 in the barrel 16 may be accomplished in various ways. For example and for simplicity, the movement of the screw 12 may be varied by the use of, for example, a cap, for example, cap 58 of FIG. 4B.

Referring again to FIG. 4, the possible movement of the sleeve 46 in the barrel 16 can be understood by realizing that the sleeve 46 may move in the direction of arrow 60 along longitudinal axis 62 of the hip screw assembly 10. The sleeve 46 defines an outer periphery 64 that is in sliding contact with large bore 66 of the barrel 16. The barrel 16 further defines a small bore 68. A shoulder 70 is formed between small bore 68 and large bore 66.

The shoulder 70 of the barrel 16 defines one limit of motion along arrow 60 of the sleeve 46. The other limit of motion of the sleeve 46 along arrow 60 is defined by face 72 of the cap 58. It should be appreciated by adjusting the position of the face 72 with respect to the hip screw assembly 10 the travel length TL of the sleeve 46 may be adjusted. The travel length TL is equal to the sleeve length SL minus the barrel length BL extending from shoulder 72 face of the cap 58.

It should be appreciated that the cap 58 may be secured to the barrel 16 in any suitable fashion. The cap 58 may, for example, be secured by fasteners, may be interferencely fit, or may be welded. For simplicity, the cap 58 may include external threads 74 which engage internal threads 76 formed in the barrel 16. While it should be appreciated that the cap 58 may be threadably adjusted such that the face 72 of the cap 58 is in a variety of positions, to fixedly secure the cap 58, the cap 58 may be secured by advancing the cap 58 until it is locked with the threads 76 of the barrel 16.

Referring again to FIGS. 4A and 4B it should be appreciated to vary the travel length TL of the screw 12 and the sleeve 46 in the hip screw assembly 10, caps of varying length may be provided. For example, as shown in FIG. 4A, a second cap 78 may be utilized, rather than first cap 58. The second cap 78 has a height H2 which is greater than the height H1 of the first cap 58. Thus, the use of the first cap 58 provides for a travel length TL1 which is greater than the travel length TL2 of the hip screw assembly utilizing second cap 78.

Figure 4C:
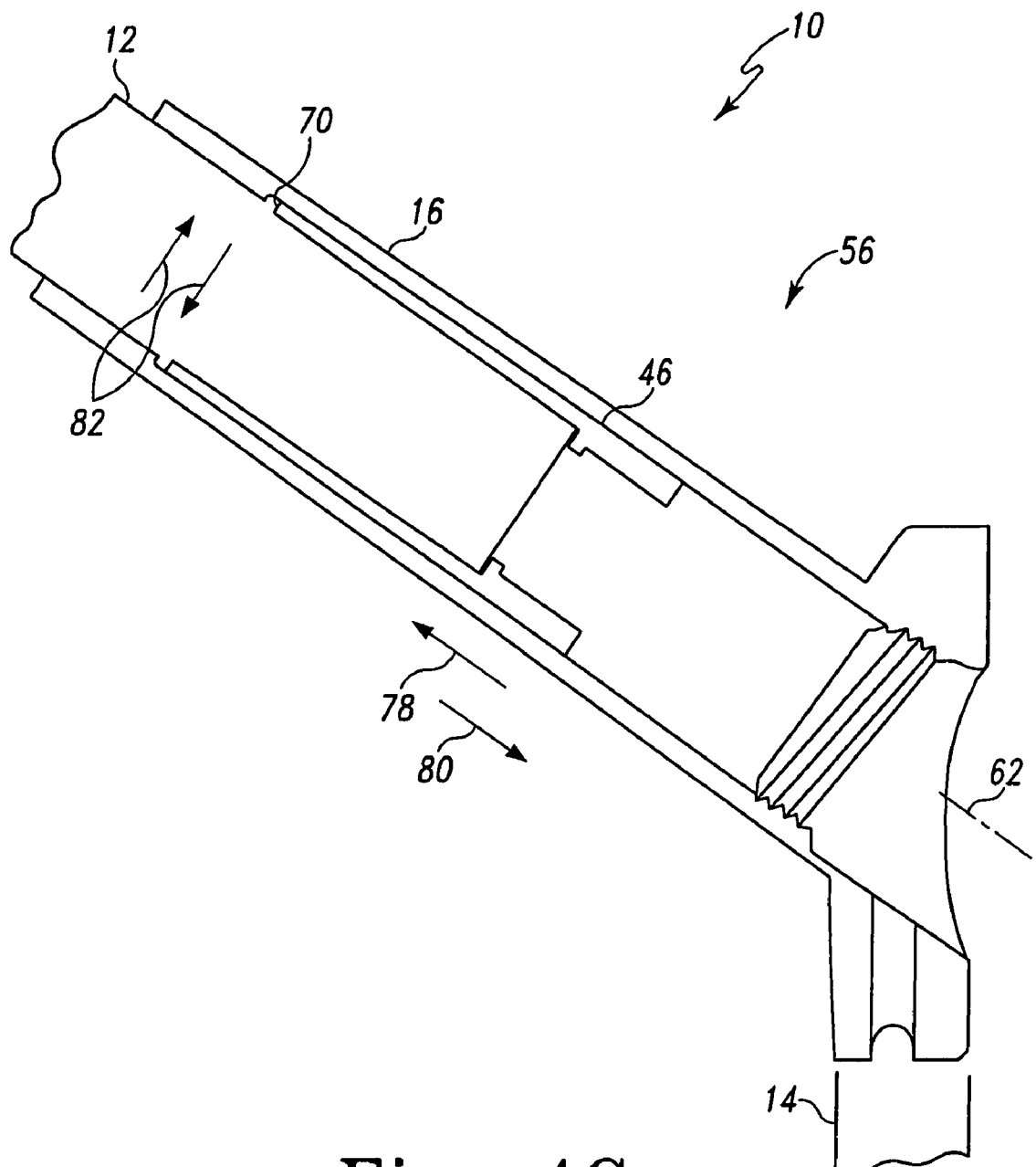
FIG. 4C is a enlarged partial plan view, partially in cross section, of the screw and barrel of the hip screw assembly of FIG. 1 without the key and key screw of FIG. 18 and without the cap of FIGS. 19-20.
Figure 4D:
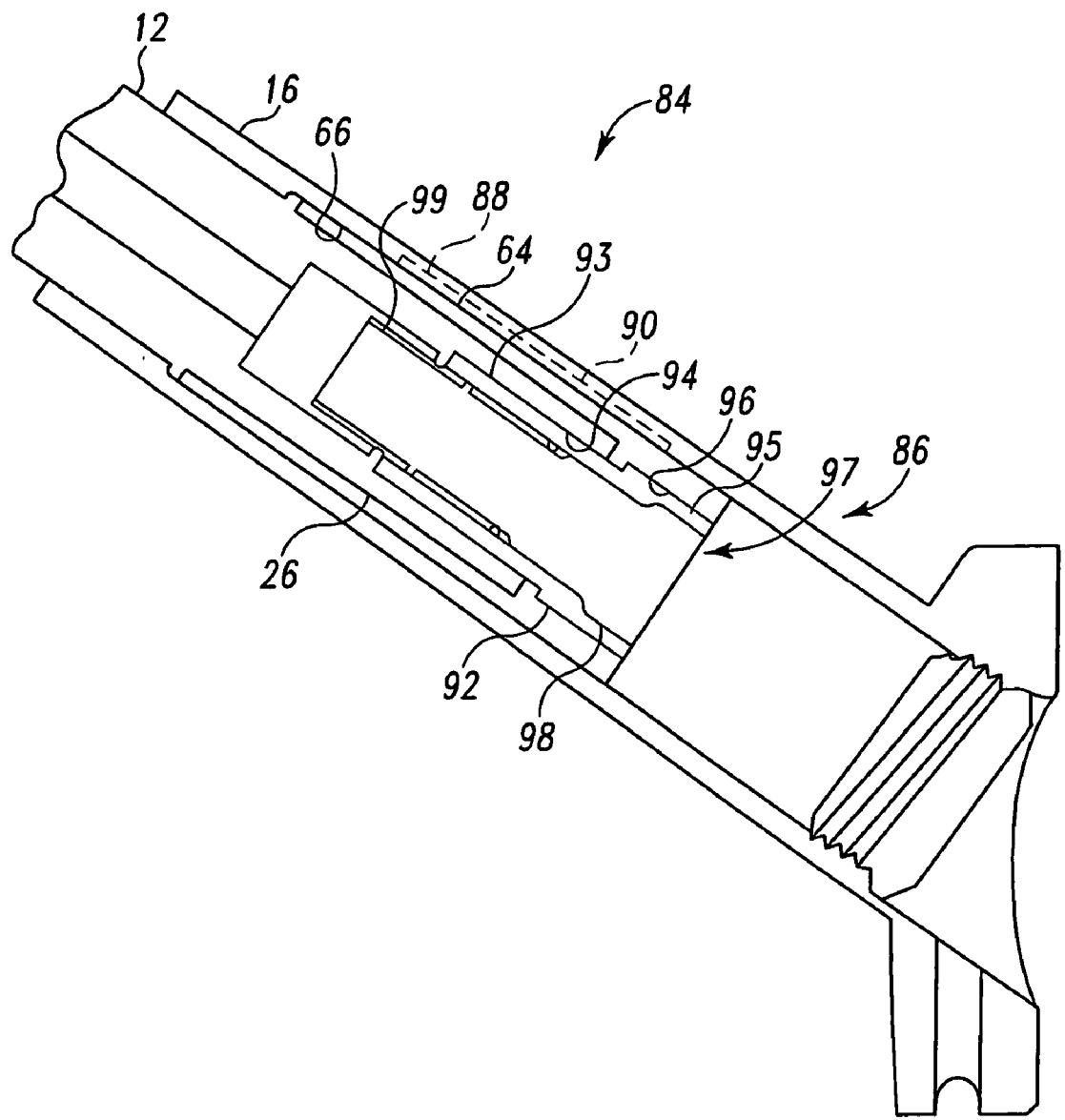
FIG. 4D is a enlarged partial plan view, partially in cross section, of the screw and barrel of the hip screw assembly of FIG. 1 without the cap of FIGS. 19-20 and including the key and key screw of FIG. 18.

Referring now to FIGS. 4C and 4D, additional arrangements that utilize the hip screw assembly 10 of the present invention are shown. As shown in FIG. 4C, the hip screw assembly 10 is shown utilizing the screw 12, the plate 14, the barrel 16 and the sleeve 46. The screw 12 is limited in motion in the direction of arrow 78 by shoulder 70 of sleeve 46. The screw 12 however is not limited in the direction of arrow 80 opposed to the arrow 78 along longitudinal center line 62. The lack of restriction in the direction of arrow 80 is permissible by not having the cap 58 in position in the barrel 16.

The screw 12 is permitted to rotate in the direction of arrows 82 with respect to the sleeve 46, as shown in FIG. 4C. It should be appreciated that the rotation of the screw 12 in the direction of arrows 82 may be undesirable. Movement of the screw 12 in the direction of arrows 82 may lead to cutout. Cutout occurs when, as the screw 12 rotates along longitudinal center line 62, cancellous bone is removed from the head of the femur causing the screw 12 to advance upwardly and medially as load is applied to the femur 2.

To minimize cutout, the screw 12 may be prohibited from significant rotation. One way to minimize the rotation of the screw 12 is to provide or angular orientation or restriction of the screw 12 with respect to the barrel 16. One such method is to provide, as shown in FIG. 4D, an angular orientation between the sleeve 46 and the barrel 16 by providing a sleeve/barrel anti-rotation feature 84. Further, the screw 12 may be prevented from rotating with respect to the sleeve 46 by providing a screw/sleeve anti-rotation feature 86.

For example, the barrel sleeve anti-rotation feature 84 may be in the form of a longitudinal groove 88 formed in barrel large bore 66 of barrel 16 which cooperates with longitudinal protrusion 90 extending from periphery 64 of sleeve 46. It should be appreciated that the barrel may include a protrusion and the sleeve include a groove. It should also be appreciated that, alternatively, a solitary longitudinal groove mating with a solitary longitudinal protrusion may be utilized. As shown in FIGS. 1 through 10, the sleeve anti-rotation feature 84 may be in the form of a plurality of spaced-apart grooves and protrusions. For example, the grooves may include opposed longitudinal grooves 88 and the protrusions may be in the form of opposed longitudinal protrusions 90.

It should be appreciated that the barrel sleeve anti-rotation feature may be in any form to prevent relative rotation of the sleeve in the barrel. For example, the sleeve or barrel may have a flat or flats that mate with corresponding raised area on the other part. The sleeve or barrel may have teeth, splines or other non round shapes as long as the sleeve and barrel have a uniform cross section so that sliding of the sleeve in the barrel is possible.

It should further be appreciated that the sleeve or the barrel themselves may not include the barrel sleeve anti-rotation feature. Such a configuration may still utilize the end cap of the present invention. It should also be appreciated that the sleeve may be fastened to the lag screw inter operatively. For example the lag screw may be assembled onto the neck of the femur first. Later the sleeve may be slid over the lag screw and place in its implanted position.

The screw/sleeve articulation feature 86 may be in the form of a key 92 which includes a key screw feature 93 in the form of a flat which mates with a screw flat feature in the form of, for example, a screw flat 94 formed on screw shank 26 of screw 12. The key 92 may further include a key sleeve feature 95 in the form of, for example, a flat that mates with a sleeve flat 96 formed in counterbore 97 of sleeve 46. While it should be appreciated that the key 92 may be secured in the hip screw assembly 10 in any suitable fashion, for example and as shown in FIG. 4D, a key screw 98 may be utilized to secure the key 92 in position. The key screw 98 may include threads 99 to secure the key screw 98 to the screw 12.

The key may be secured in position in any suitable way. For example a key may be secured by another fastener in place of the key screw. For example the key may be secured by a pin with a detent, a pin with an interference fit, bayonet connection, or a snap fit etc. Alternatively the key could be captive to the lag screw. The key could screw, snap, or otherwise connect directly to the lag screw. The key could be deployed interoperatively and may for example be secured to the lag screw after the lag screw has been place in the femur.

Figure 5:
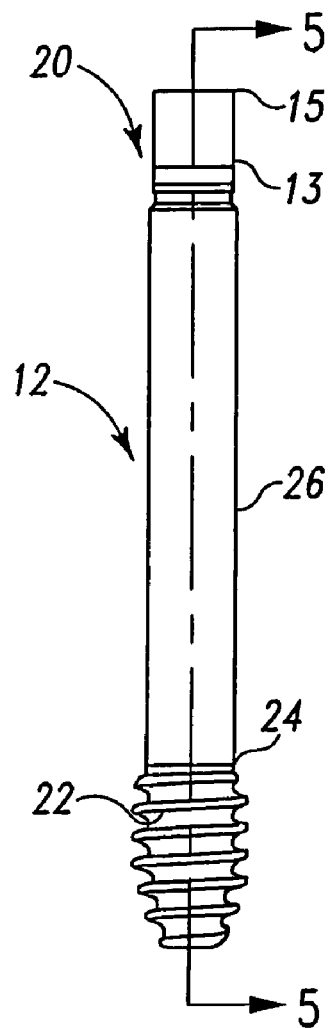
FIG. 5 is a plan view of the screw of the hip screw assembly of FIG. 1.

Referring now to FIGS. 5 thru 8, the compression screw 12 is shown in greater detail. Referring now to FIG. 5, the compression screw 12 includes the shank 26 as well as threads 22 which extend from end 24 of the shank 26. The compression screw 12 includes a portion 20 which is fitted in sleeve 46 of the compression hip screw (see FIGS. 12 and 13). The entire shank 24 may receive the sleeve 46. As shown in FIG. 5, the shank 26 may include a sleeve receiving surface 13 which matingly fits with the sleeve 46. The sleeve receiving surface 13 may be positioned at second end 15 of the compression screw 12.

Figure 6:
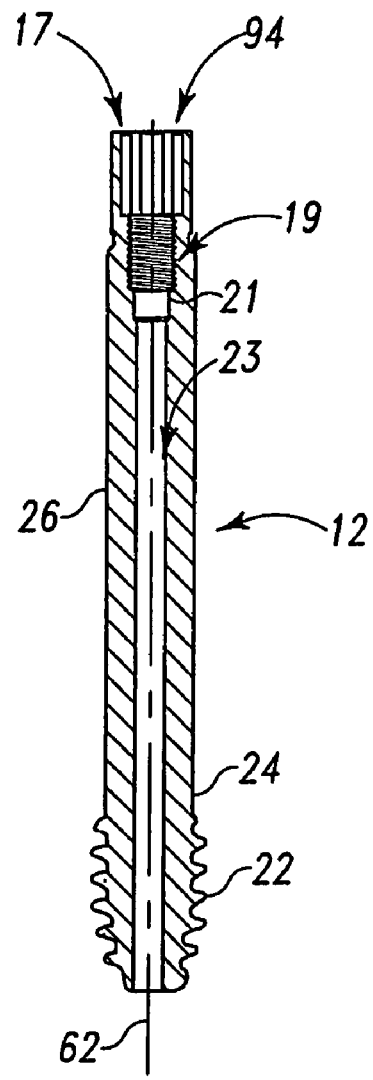
FIG. 6 is a cross sectional view of FIG. 5 along the line 6-6 in the direction of the arrows.

Referring now to FIG. 6, the compression screw 12 may include a large counterbore 17 onto which internal flats 94 are formed. While a single internal flat 94 or a similar angular orientation feature in the form of for example a protrusion, teeth, or splines may be utilized to angular orient the screw 12 with the key 92. While a single flat 94 may be utilized, it should be appreciated that a pattern of flats 94 may be utilized. For example, flats 94 may form a polygon pattern. For example, a triangular, rectangular, pentagonal, or octagonal shape may be used. For example and as is shown in FIG. 6, the internal flats 94 form a hexagonal pattern. The compression screw 12 may further include a small counterbore 19 that is positioned internally from the large counterbore 74. The small counterbore 19 may include internal threads 21 for receiving the key screw threads 99 of the key screw 98 (see FIG. 17). The compression screw 12 may include a longitudinal opening 23 positioned centrally along longitudinal center line 62 of the screw assembly 10.

Figure 7:
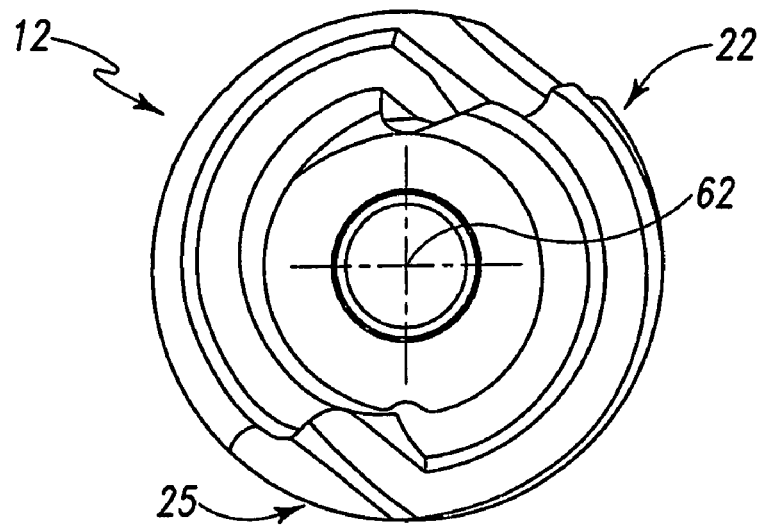
FIG. 7 is an end view of the screw of the hip screw assembly of FIG. 1.

Referring now to FIG. 7, the screw 12 may be a self-tapping screw and include a self-tapping feature 25 for easily positioning the screw 12 into the femur 2. The self-tapping feature 25 may minimize the trauma and damage to the femur during assembly of the screw 12.

Figure 8:
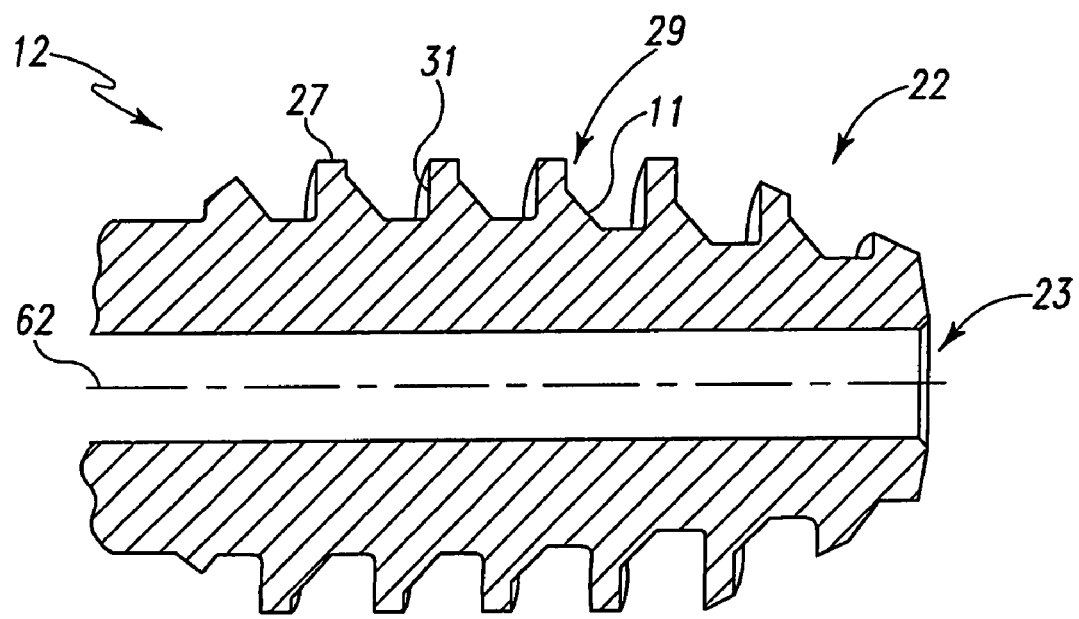
FIG. 8 is a partial cross sectional view of FIG. 7 along the line 8-8 in the direction of the arrows.

Referring now to FIG. 8, the threads 22 of the screw 12 are shown in greater detail. The threads 22 may, as shown in FIG. 8, be truncated to minimize cutout of the threads and to minimize the backing out of the screw as well. The threads 22 may include a truncated crest 27. The threads 22 may further include a leading flank 29 which includes a tapered or angular portion 11, as well as, a trailing flank 31 which is normal to longitudinal axis 62 of the screw 12. The perpendicular trailing flank 31 and the truncated crest 27 serve to minimize cutout of the screw 12.

The screw 12 may be made of any suitable durable material and may for example be made of a metal. If made of a metal, the screw 12 is made of a biocompatible material, for example a cobalt chromium alloy, a stainless steel alloy or a titanium alloy.

Figure 9:
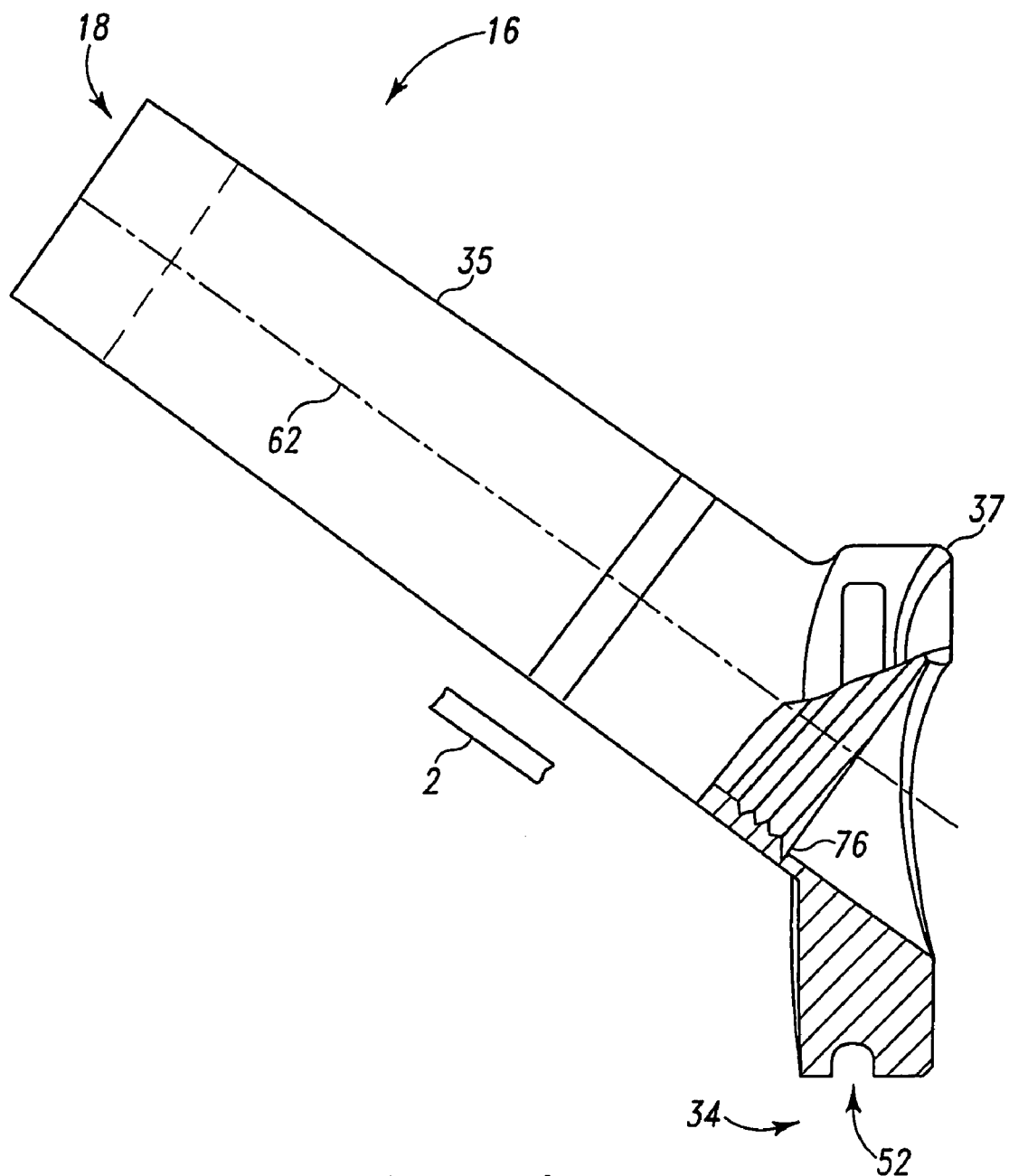
FIG. 9 is a plan view, partially in cross section, of the barrel of the hip screw assembly of FIG. 1.
Figure 10:
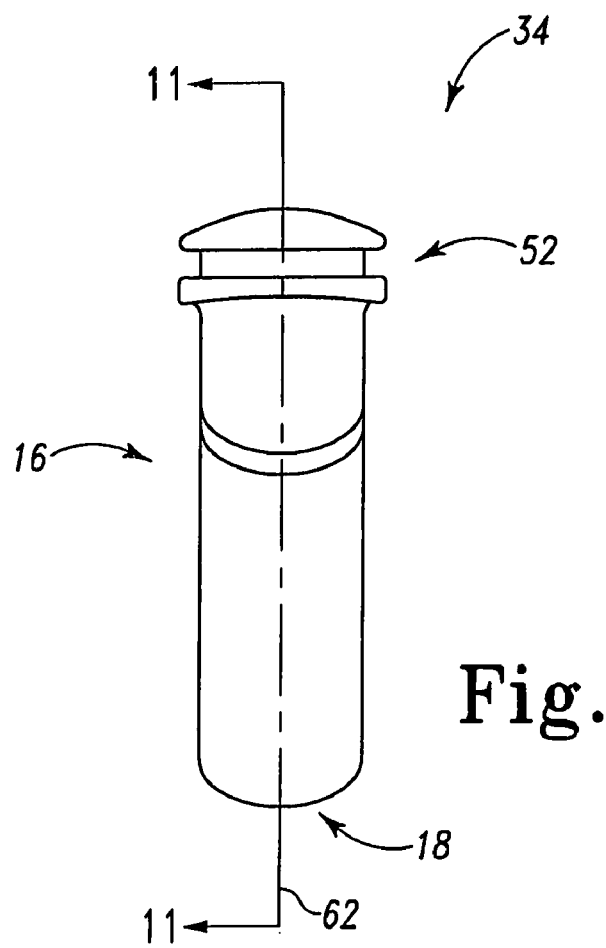
FIG. 10 is an end view of the barrel of FIG. 9.

Referring now to FIGS. 9, 10 and 1 the barrel 16 is shown in greater detail. The barrel 16 includes a stem portion 35 which is fitted into the femur 2 as well as a flange 37. The flange 37 includes the channel 52 which cooperates with the channel 36 of the plate 14 to form the barrel plate connector 34.

As shown in FIG. 10 the barrel 16 includes a longitudinal opening 18 which is centrally positioned along longitudinal center line 62 of the screw assembly 10.

Figure 11:
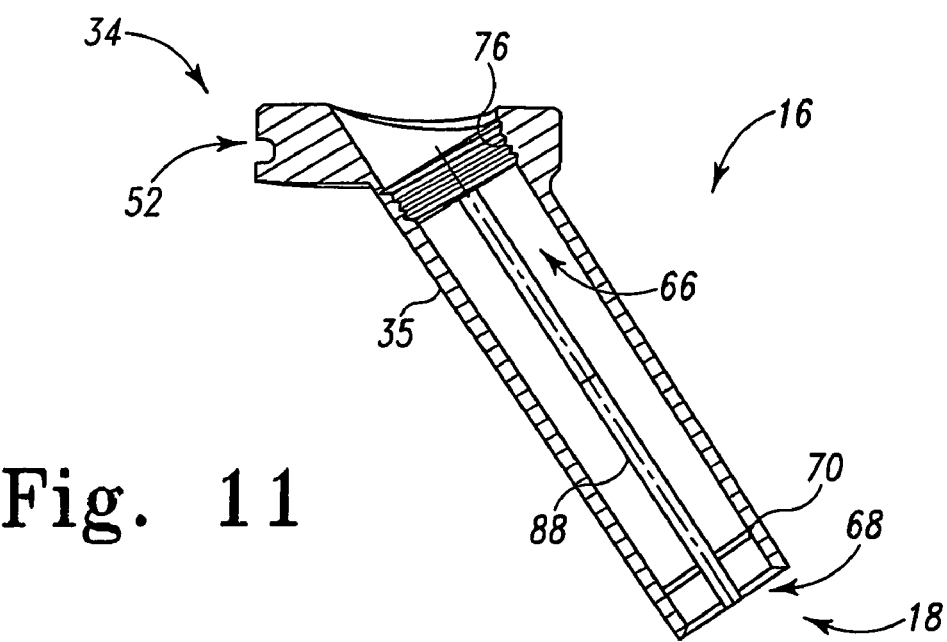
FIG. 11 is a cross sectional view of FIG. 10 along the line 11-11 in the direction of the arrows.

Referring now to FIG. 11 the barrel 16 includes the large bore 66, as well as a small bore 68. The transition between the large bore 66 and the small bore 68 defines shoulder 70. The barrel 16 further defines longitudinal groove 88 formed in large bore 66 of the barrel 16. While the longitudinal groove 88 may be a solitary longitudinal groove, it should be appreciated that the shape and size of the longitudinal groove 88 preferably mates that of the protrusion 90 of the sleeve 46 (see FIGS. 12 and 13). The longitudinal groove 88 may be in the form of a pattern of longitudinal grooves and may, as shown in FIGS. 9, 10 and 11, include a pair of opposed longitudinal grooves 88.

Figure 12:
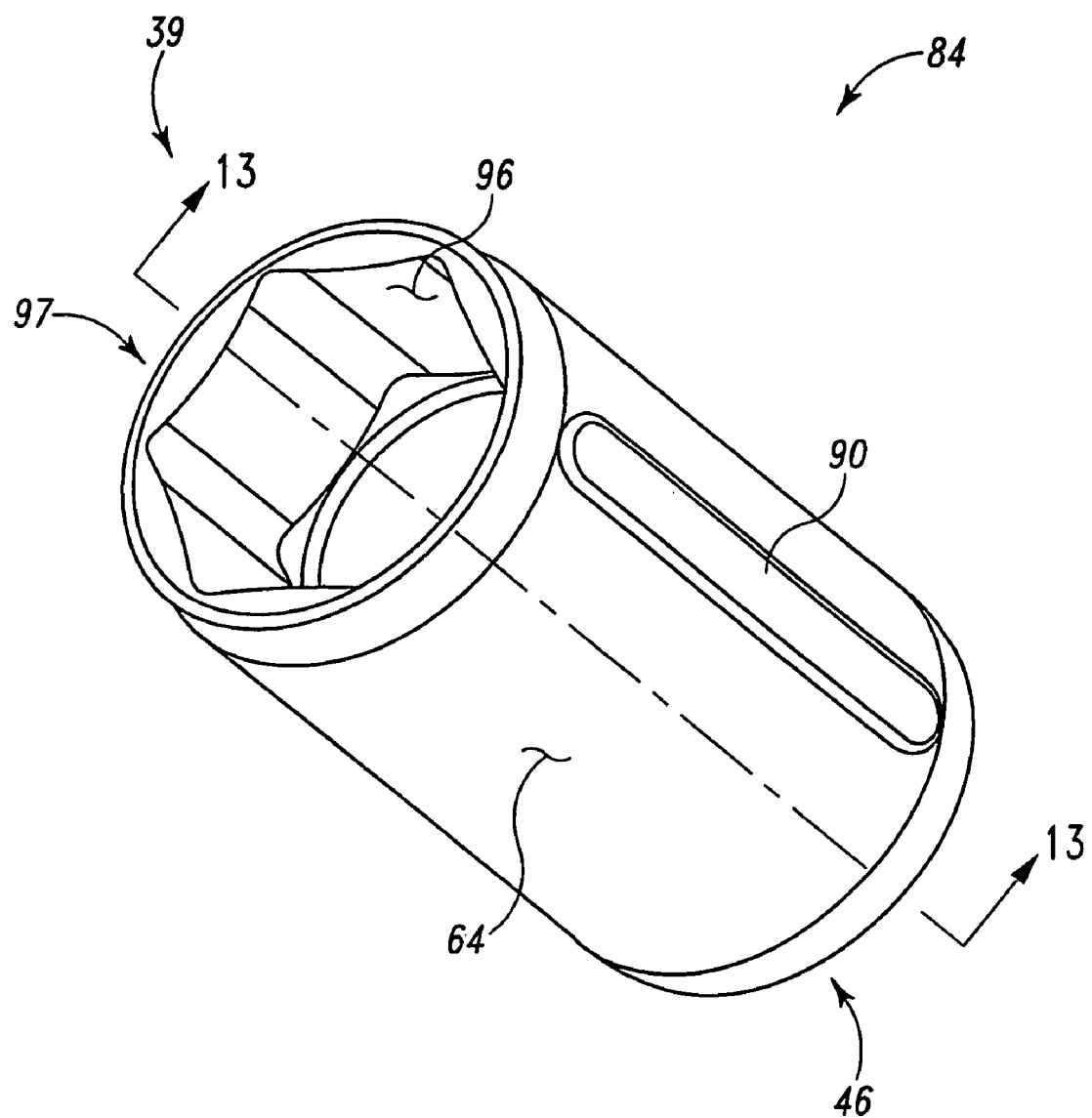
FIG. 12 is a perspective view of the sleeve of the hip screw assembly of FIG. 1.
Figure 13:
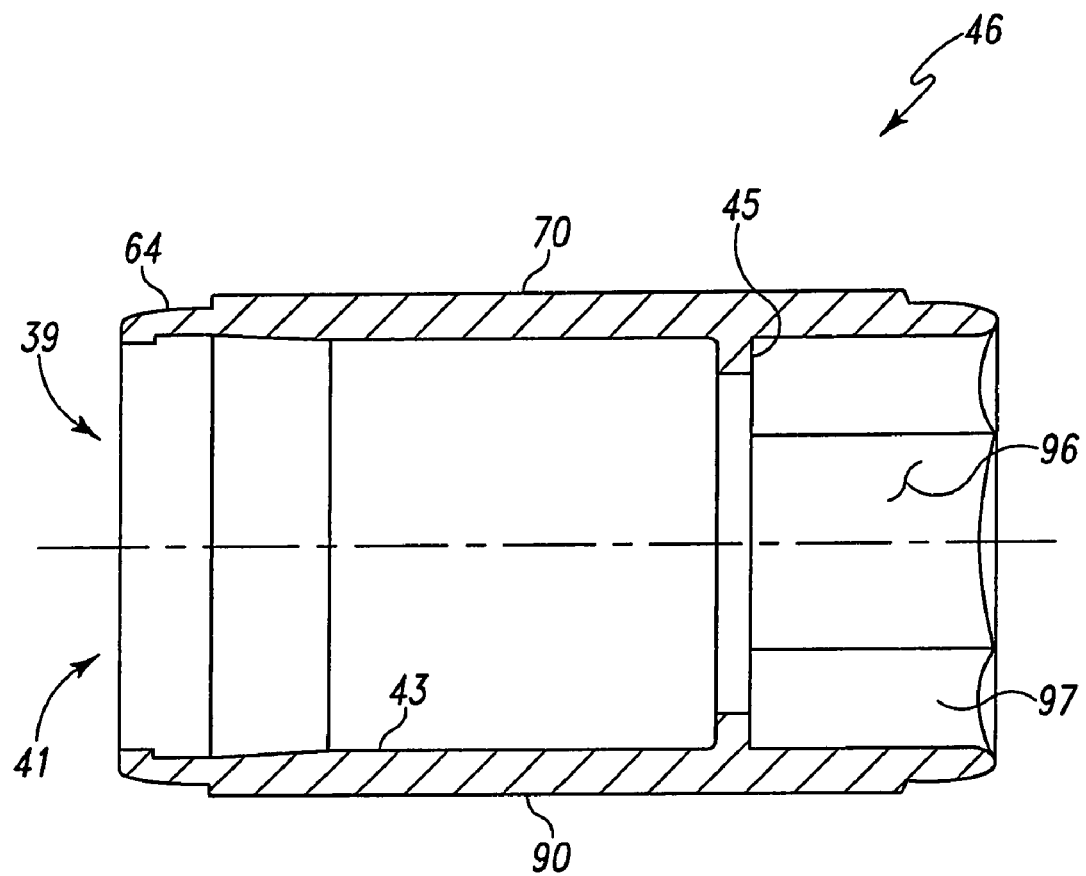
FIG. 13 is a cross sectional view of FIG. 12 along the line 13-13 in the direction of the arrows.

Referring now to FIGS. 12 and 13, the sleeve 46 is shown in greater detail. The sleeve 46 includes a longitudinal opening 39 for receiving at least a portion of the shank 26 of the compression screw 12 of FIGS. 5 through 8. The sleeve 46 includes counterbore 97 of the sleeve 46. The counterbore 97 defines an orientation feature 96 in the form of a flat. While a solitary flat 96 may be included in the sleeve 46, preferably, the orientation feature 96 of the sleeve 46 mates with the sleeve/key feature 95 of the key 92.

For example and as shown in FIG. 46 the orientation feature 96 is in the form of a plurality of evenly spaced about flats. It should be appreciated that a polygon pattern of flats, for example a triangular, square, pentagonal, or octagonal pattern of flats may be utilized. For simplicity, the flats 96 may form, as shown in FIG. 12, a hexagonal pattern.

As shown in FIG. 12, the sleeve 46 includes an angular orientation feature 84 in the form of a groove or protrusion 90. While a solitary longitudinal protrusion 90 may be utilized it should be appreciated that the angular orientation feature 84 of the barrel/sleeve anti-rotation feature should include a sleeve orientation feature 90 which mates with a barrel orientation feature 88 of the barrel 16 of FIGS. 10 through 11. For example and as shown in FIG. 12, the sleeve angular orientation feature 90 is in the form of a protrusion. While a solitary protrusion 90 may be utilized it should be appreciated that a pattern of spaced apart protrusions 90 may be utilized. As shown in FIG. 12, two opposed protrusions 90 extend outwardly from periphery 64 of the sleeve 46.

Referring now to FIG. 13 the sleeve 46 includes the longitudinal opening 39. The longitudinal opening 39 of the sleeve 46 includes counterbore 97 as well as an opposed counterbore 41 which defines a screw shank receiving bore 43. The screw shank receiving bore 43 and the counterbore 97 are separated by for example shoulder 45. The screw shank receiving bore 43 is designed to receive sleeve receiving surface 13 of the screw 12 (see FIG. 5).

Figure 14:
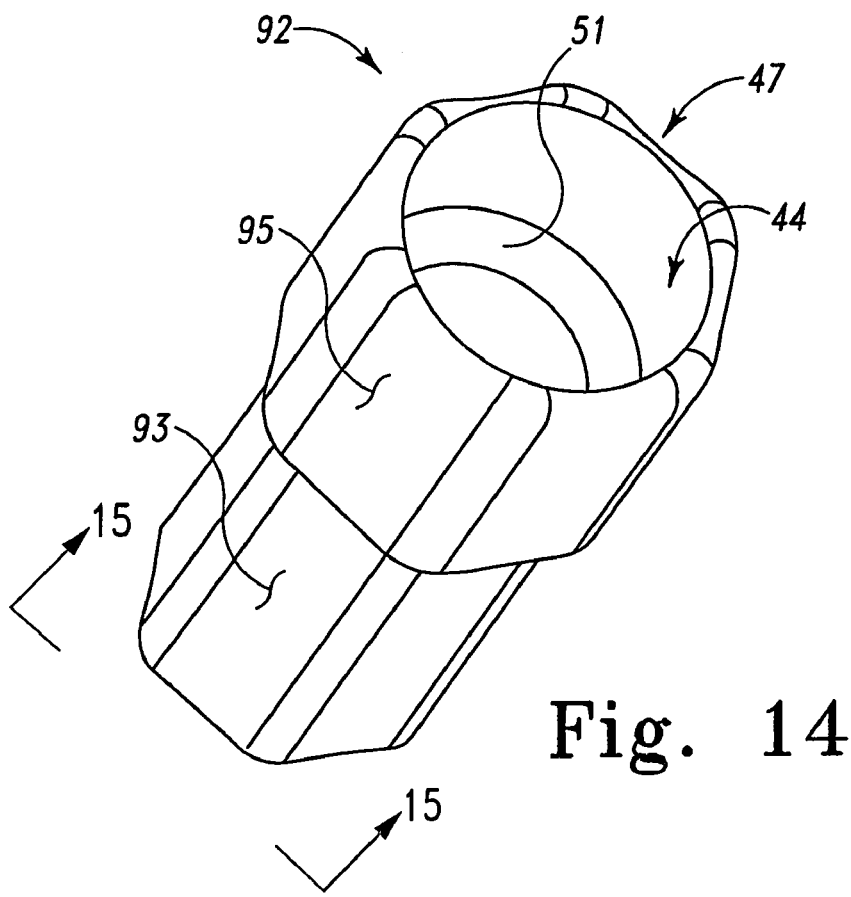
FIG. 14 is a perspective view of the key of the hip screw assembly of FIG. 1.
Figure 15:
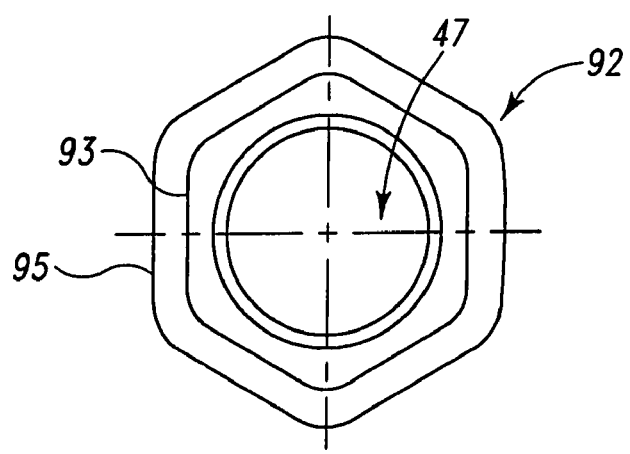
FIG. 15 is a view of FIG. 14 along the line 15-15 in the direction of the arrows.

Referring now to FIGS. 14 and 15 the key 92 is shown in greater detail. The key 92 includes the first orientation feature 93 in the form of an external flat. As shown in FIGS. 14 and 15, the flats 93 may be in the form of a plurality of spaced apart flats. The flats 93 may be in a polygon pattern, for example a triangular pattern, a square pattern, or an octagonal pattern. For example and as shown in FIGS. 14 and 15, the flats 93 are in a hexagonal pattern. Similarly, the second angular orientation feature 95 may be in the form of flats 95. The flats 95 may be a series of spaced apart flats. For example, the flats 95 may be uniformly spaced apart in, for example, a polygon pattern. For example, the flats may be in the form of a triangular, rectangular, pentagonal or octagonal pattern. For example and as shown in FIGS. 14 and 15, the flats 95 are in the form of a hexagonal pattern.

Figures 16, 17:
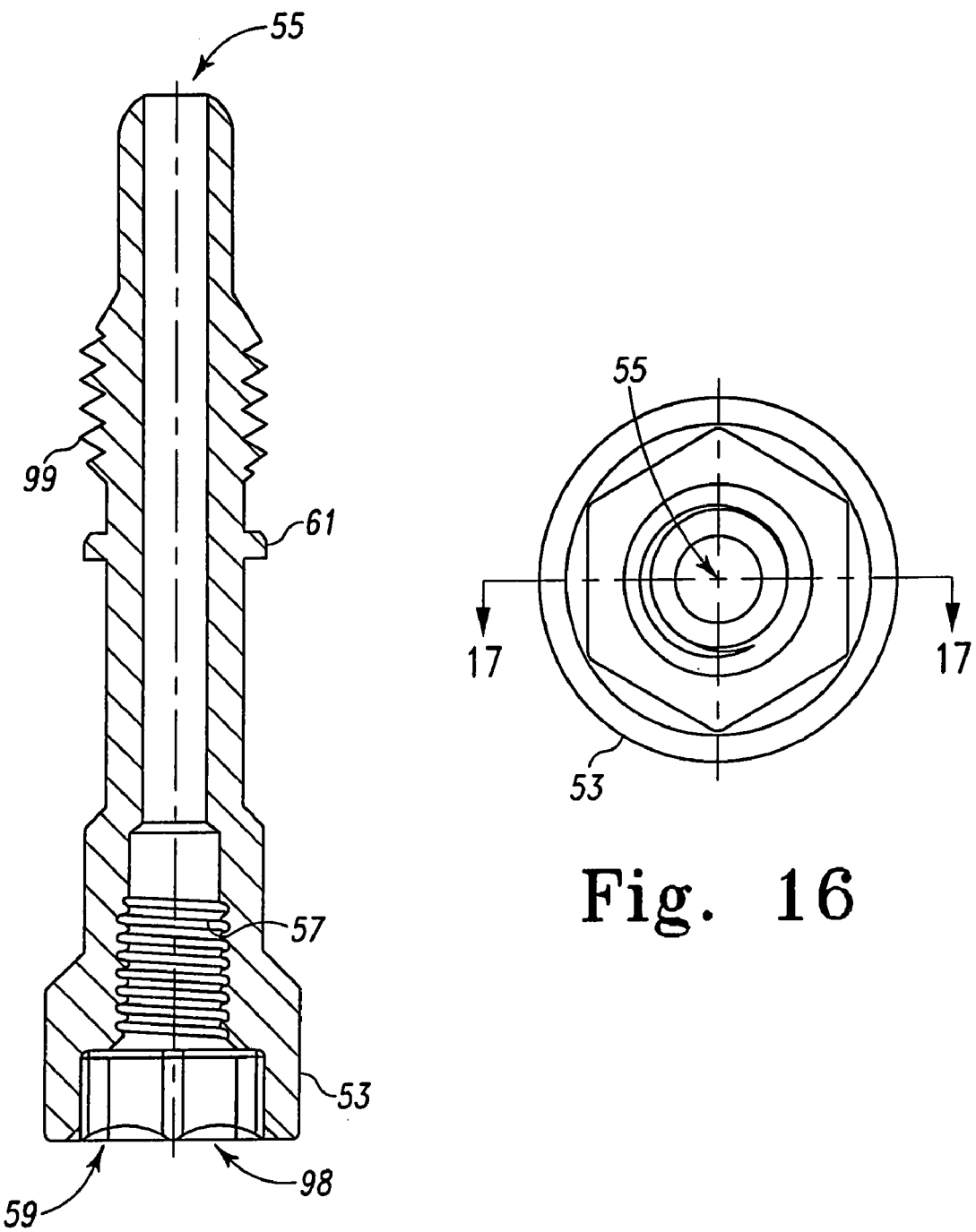
FIG. 16 is a end view of the key screw of the hip screw assembly of FIG. 1.
FIG. 17 is a cross sectional view of FIG. 16 along the line 17-17 in the direction of the arrows.

The key 92 includes a longitudinal opening 47 for receiving key screw 98 (see FIGS. 16 and 17). The longitudinal opening 47 includes a large counterbore 49 extending from shoulder 51 of the key 92. The counterbore 49 is adapted to receive the key screw 98. The counterbore 49 and longitudinal opening 47 define the shoulder 51 positioned between the counterbore 49 and the opening 47.

Referring now to FIGS. 16 and 17 the key screw 98 is shown in greater detail. As shown in FIG. 16 the key screw 98 includes a large outer periphery 53 which is in clearance with large counterbore 49 of the key 92 of FIGS. 14 and 15.

Referring now to FIG. 17 the key screw 98 includes the external threads 99 for cooperation with internal threads 21 formed in small counterbore 19 of the sleeve 12 of FIGS. 5 through 8. The key screw 98 further includes a longitudinal opening 55. The key 98 also includes internal threads 57 and internal flats 59. The internal threads 57 and internal flats 59 may be utilized in assembly and disassembly of the key screw 98 into the hip screw assembly 10. The key screw 98 may further include a rib 61 for securing the key screw 98 to the key 92 (see FIG. 18).

The key 92 and the key screw 98 may be made of any suitable durable material and may for example be metal. If made of a metal, the key 92 and the key screw 98 may be made of, for example, a cobalt chromium alloy, a stainless steel alloy, or a titanium alloy.

Figure 17A:
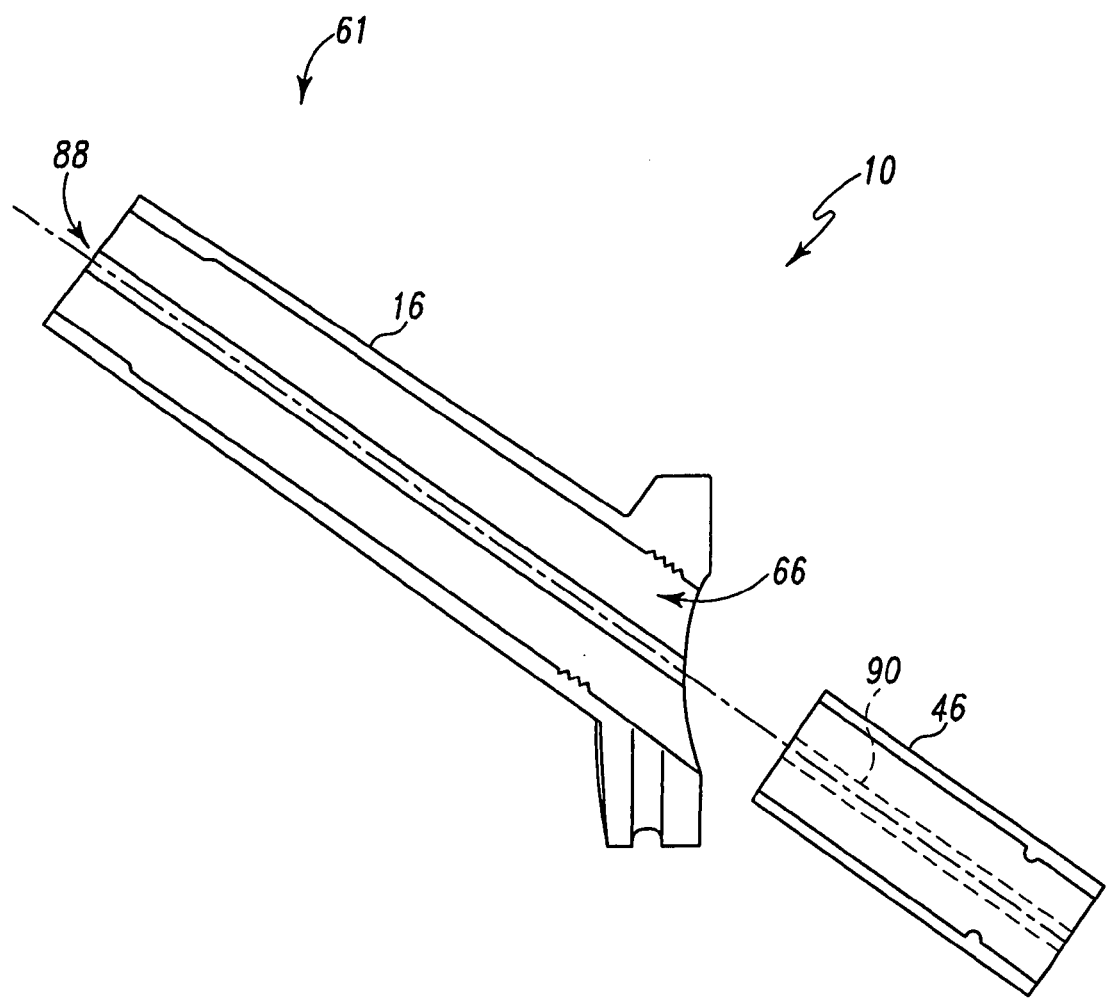
FIG. 17A is an exploded plan view, partially in cross section, of the barrel and sleeve subassembly of the hip screw assembly of FIG. 1.

Referring now to FIGS. 17A through 20A, the hip screw assembly 10 is shown in various stages as it is assembled onto the femur 2. For example, and referring now to FIG. 17A, the barrel 16 may be pre-assembled onto the sleeve 46. As shown in FIG. 17A, the sleeve 46 is assembled into the barrel 46 by placing the outer periphery 64 of the sleeve 46 into the large bore 66 of the barrel 16. The sleeve 46 is angularly oriented until the protrusions 90 of the sleeve 46 are in alignment with the grooves 88 formed in the large bore 66 of the barrel 16.

Figure 17B:
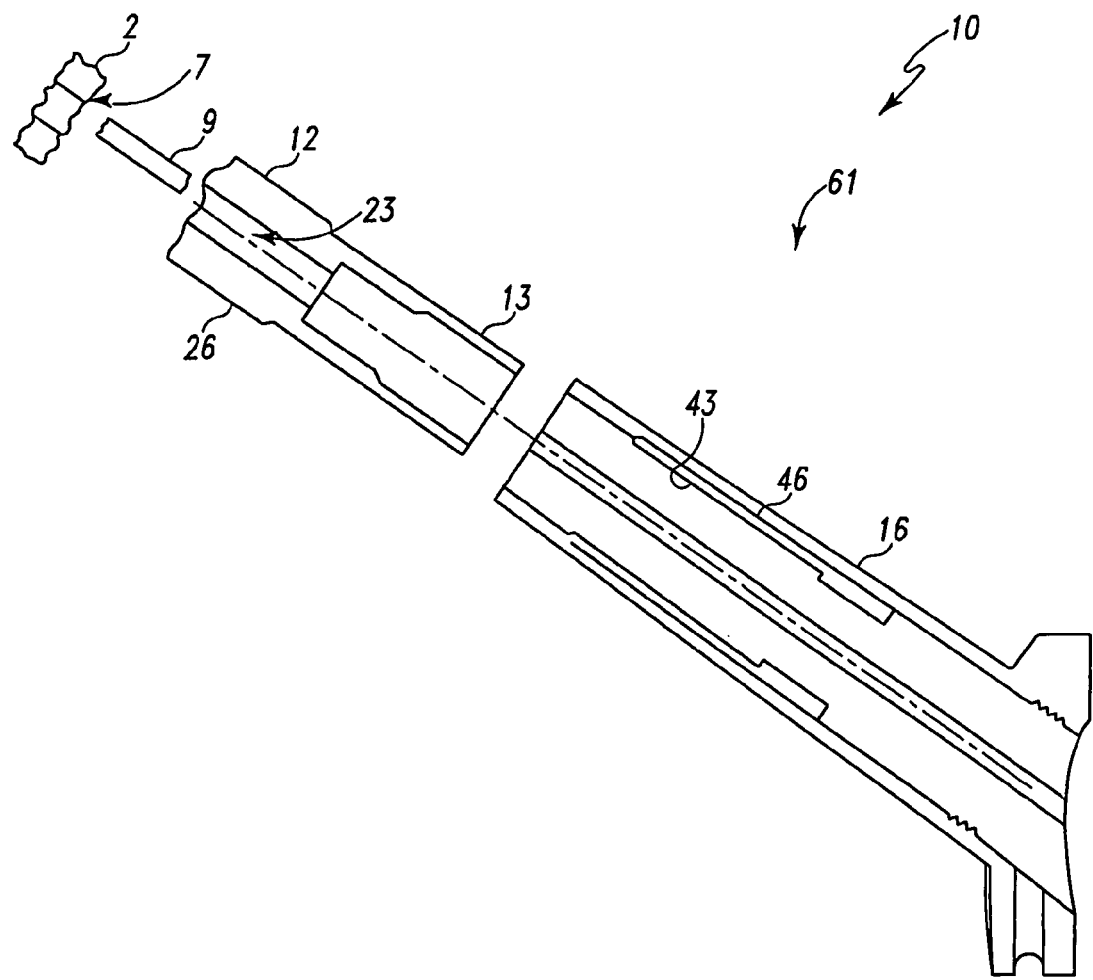
FIG. 17B is another partial exploded plan view, partially in cross section, of the barrel, sleeve, and screw subassembly of the hip screw assembly of FIG. 1.

Referring now to FIG. 17B, the barrel 16 and sleeve 46 have been pre-assembled to form sleeve/barrel assembly 61. The sleeve/barrel assembly 61 may then be assembled onto screw 12. As shown in FIG. 17B, the screw 12 is first positioned into the femur 2. A pilot hole 7 may be formed in the femur 2 and a guide pin 9 may be positioned in the hole 7. The longitudinal opening 23 formed in the screw 12 may be fitted into pin 9 to assist in positioning the screw 12 in a proper position.

As shown in FIG. 17B, the sleeve/barrel assembly 61 is assembled onto the screw 12 by aligning the shank screw receiving bore 43 of the sleeve 46 with the sleeve receiving surface 13 of the shank 26 of the screw 12.

Figure 17C:
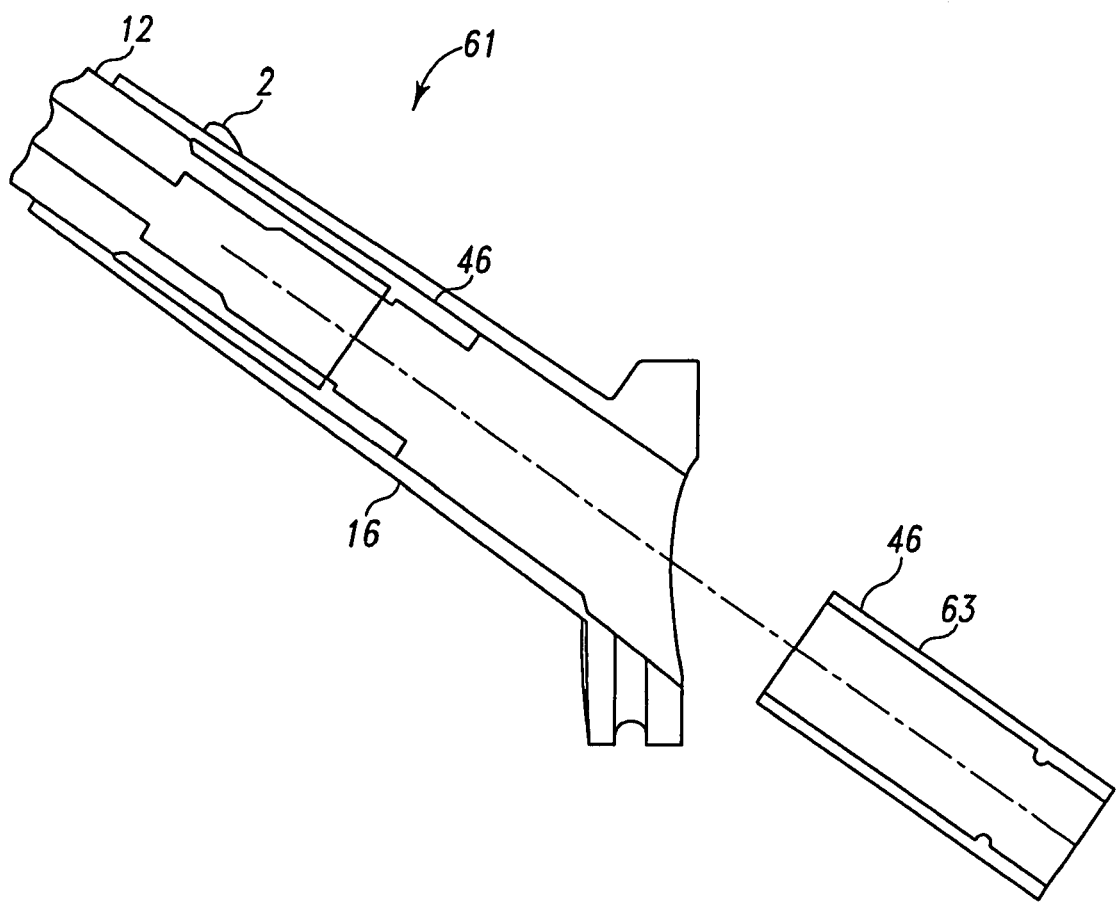
FIG. 17C is a partial exploded plan view, partially in cross section, of the barrel, sleeve, and screw subassembly of the hip screw assembly of FIG. 1.

Referring now to FIG. 17C the sleeve/barrel assembly 61 is shown in position in the femur 2 with the sleeve/barrel assembly 61 positioned over a portion of the screw 12. It should be appreciated that as shown in Phantom as 63, the sleeve 46 may be assembled onto the barrel 16 after the barrel 16 has been positioned over the screw 12.

Figure 18:
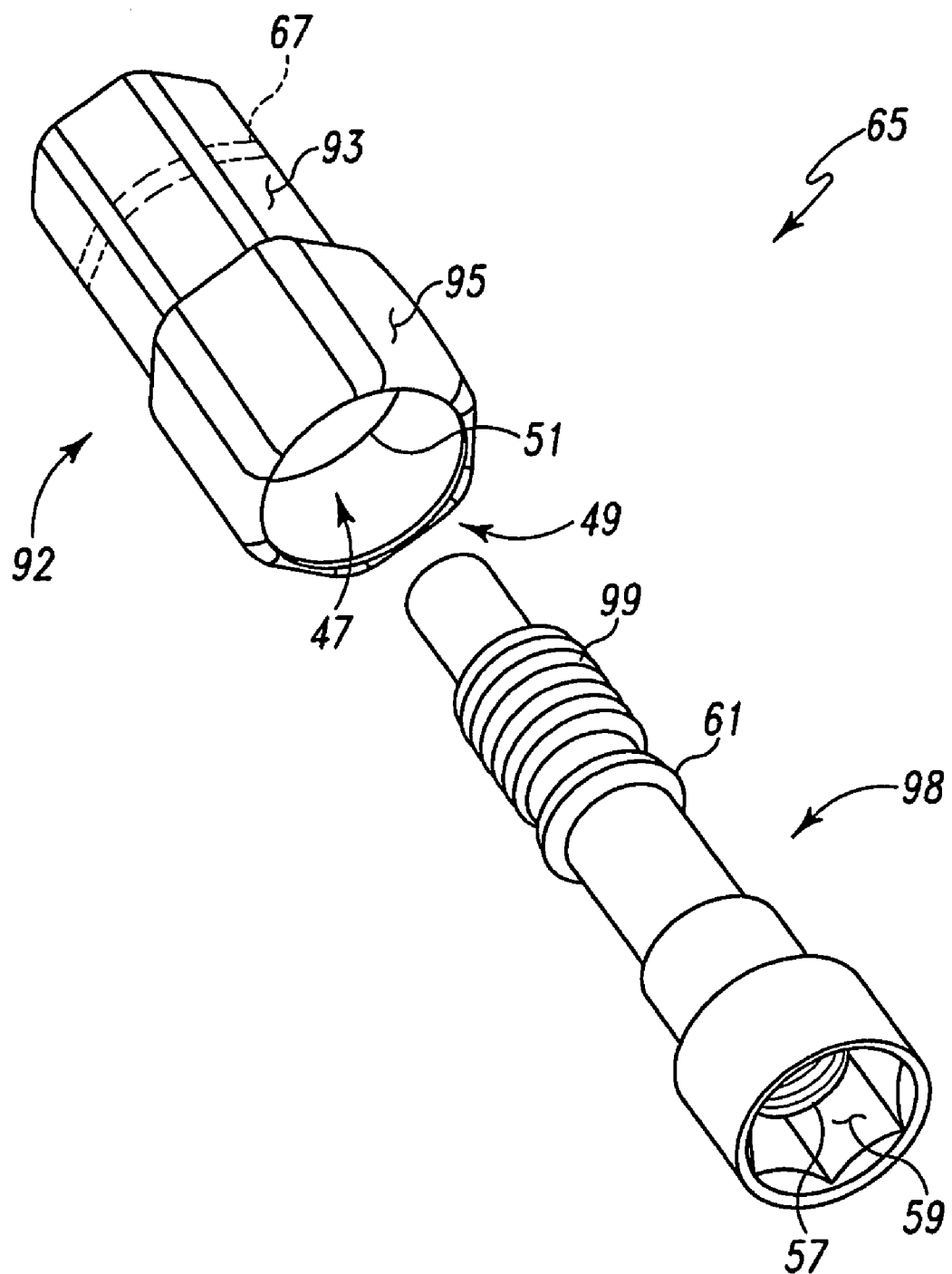
FIG. 18 is an exploded perspective view of the key and key screw subassembly of the hip screw assembly of FIG. 1.
Figure 18A:
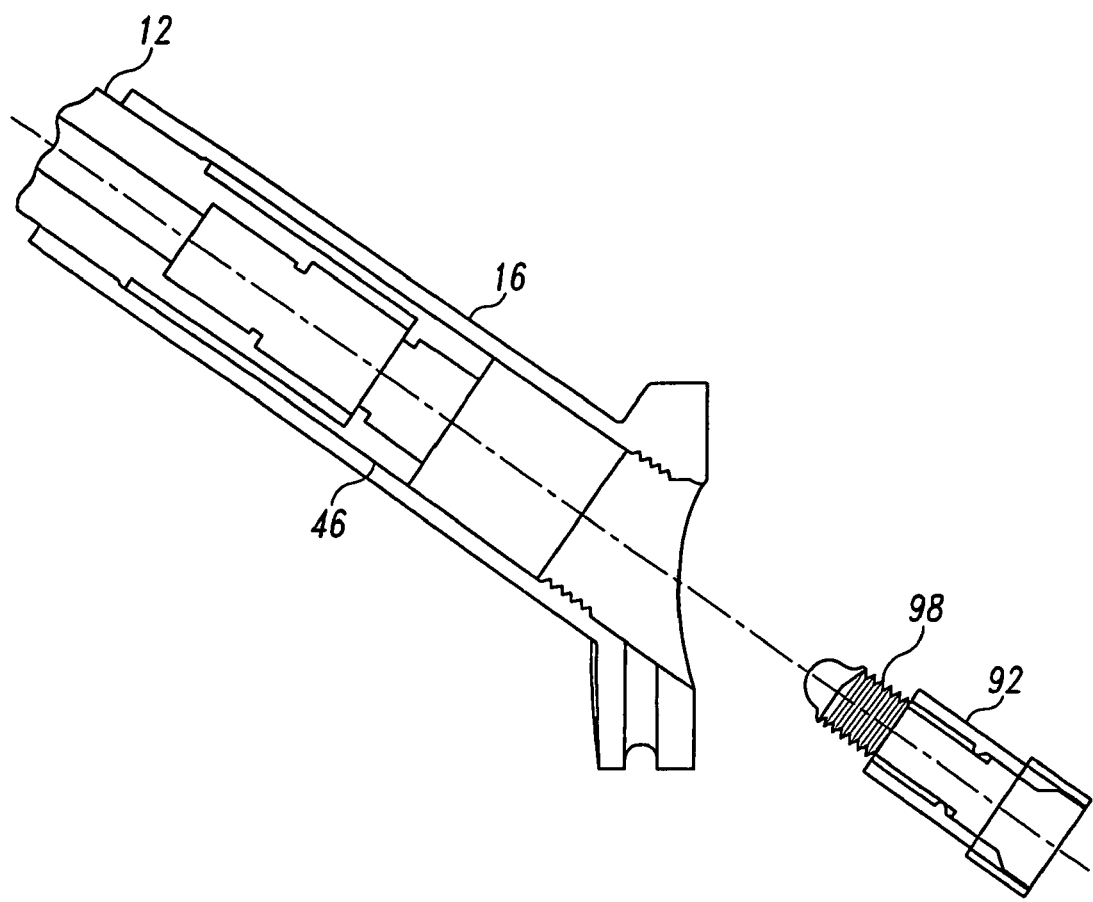
FIG. 18A is a partial exploded plan view, partially in cross section, of the barrel, sleeve, and screw subassembly and the key and key screw subassembly of the hip screw assembly of FIG. 1.

Referring now to FIG. 18, the key 92 is shown in alignment with the key screw 98 for assembly of the key screw 98 into the key 92 to form key/key screw subassembly 65. The key/key screw sub-assembly 65 includes key 92 as well as key screw 98. To assemble the key screw 98 onto the key 92, the external threads 99 of the key screw 98 are positioned in longitudinal opening 47 of the key 92. The rib 61 of the key screw 98 fits with inwardly extending shoulder 67 extending into opening 47 of the key 92. The inwardly extending shoulder 67 and the rib 62 serve to interlock the key 92 and the key screw 98 to form the key screw assembly 65.

Figure 19:
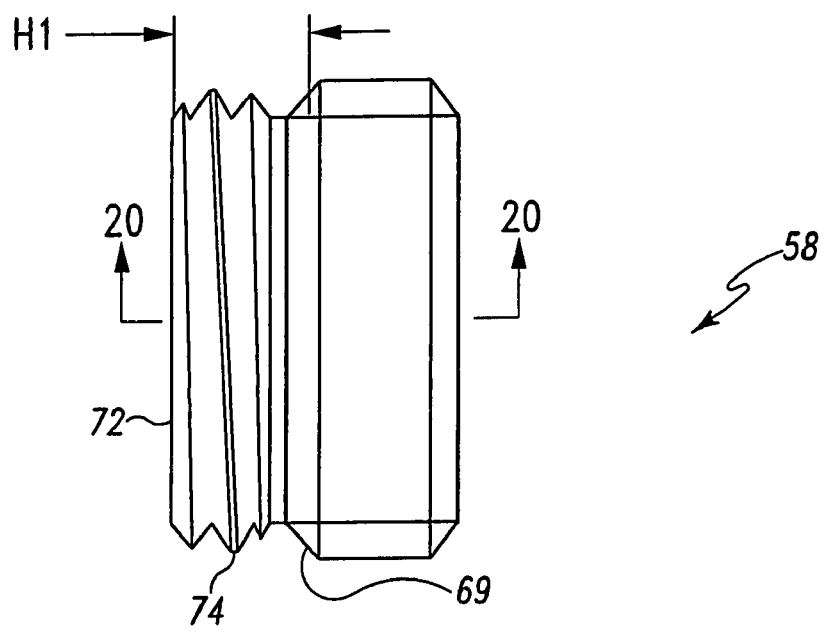
FIG. 19 is a plan view of the cap of the hip screw assembly of FIG. 1.
Figure 20:
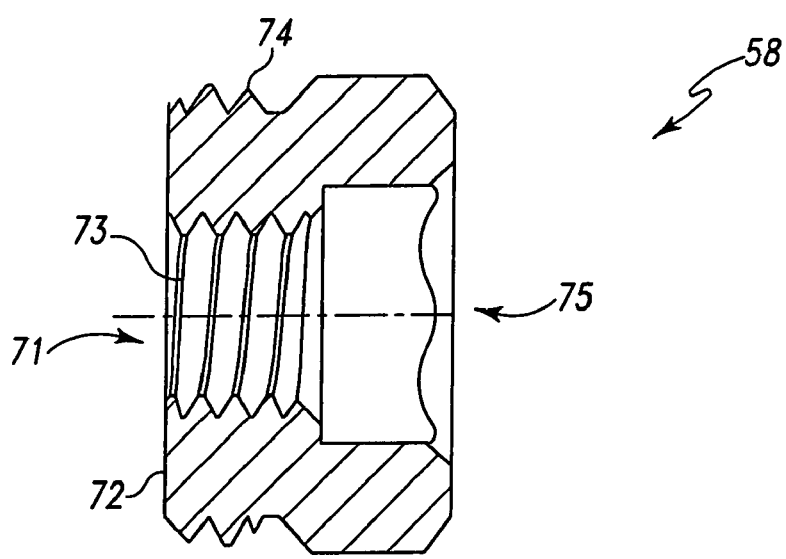
FIG. 20 is a cross sectional view of FIG. 19 along the line 20-20 in the direction of the arrows.
Figure 20A:
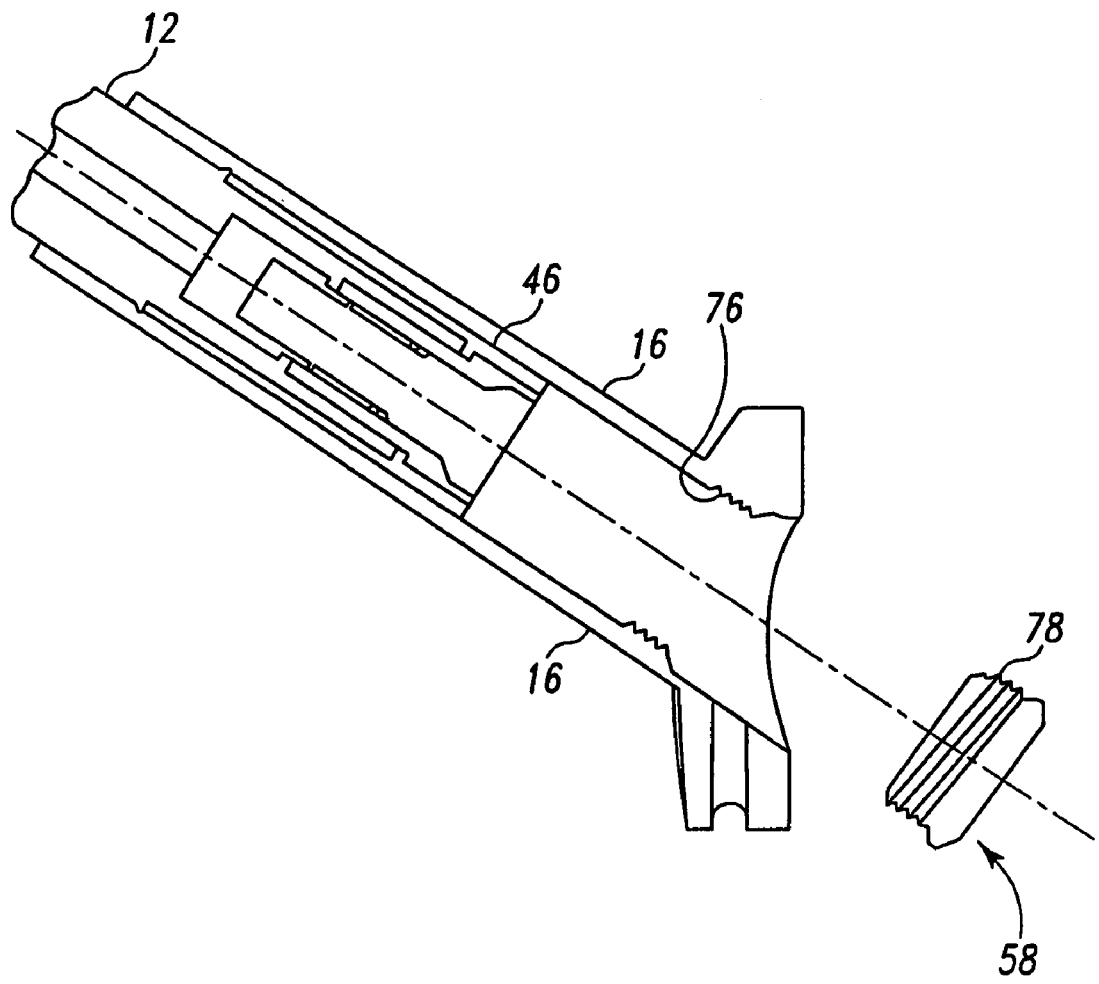
FIG. 20A is a partial exploded plan view, partially in cross section, of the barrel, sleeve, screw, key and key screw subassembly and the cap of the hip screw assembly of FIG. 1.

Referring now to FIGS. 19 and 20, the cap 58 is shown in greater detail. The cap 58 includes external threads 74 for cooperation with internal threads 76 of the barrel 16 (see FIGS. 8, 9, and 10). The cap 58 defines dimension H1 extending from face 72 of the cap 58 to shoulder 69 of the cap 58. The shoulder 69 represents an end of the external threads 74.

Referring now to FIG. 20, the cap 58 may further include a longitudinal opening 71. The cap 58 may define internal threads 73 as well as an internal flat 75 which may form an internal hexagonal pattern. The internal thread 73 and the internal flat 75 may assist in assembling and disassembling the cap 58 from the hip screw assembly 10.

Figure 21:
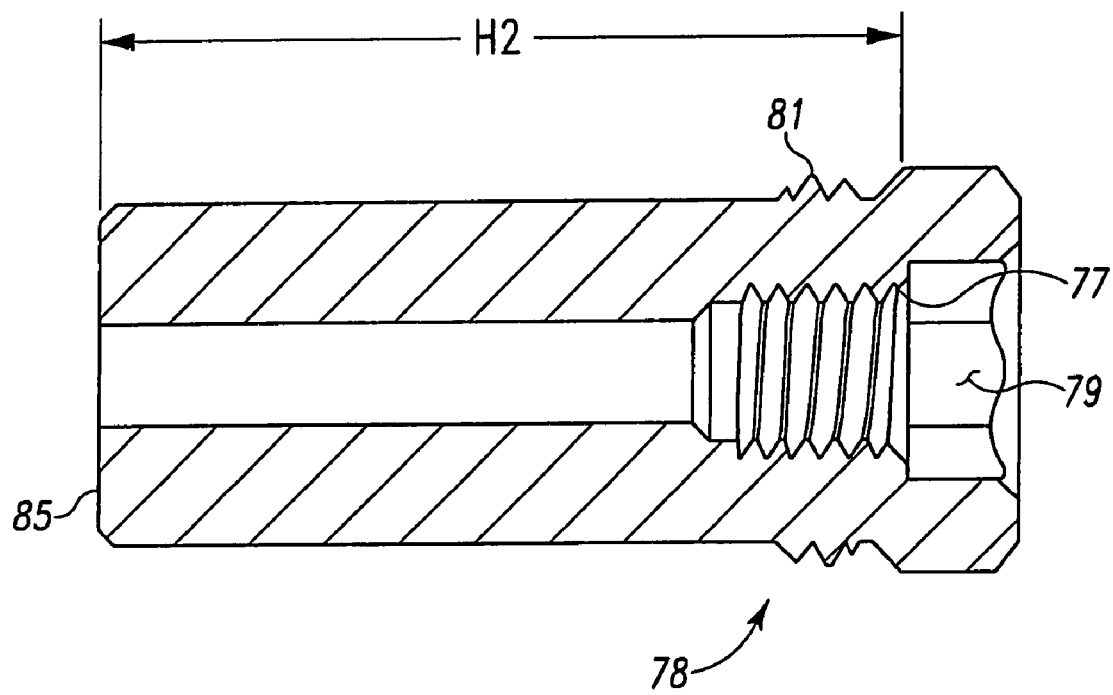
FIG. 21 is a cross sectional view of an alternate cap for use with the hip screw assembly of FIG. 1 according to another embodiment of the present invention.

Referring now to FIG. 21, second cap 78 is shown in greater detail. The second cap 78, similarly to the first cap 58, may include internal threads 77, as well as, internal flats 79. The internal threads 77 and the internal flats 79 may be utilized in assembly and disassembling the cap 78 from the hip screw assembly 10. The second cap 78 may include external threads 81 for cooperation with internal threads 76 of the barrel 16. The cap 78 may define a shoulder 83 which defines a dimension H2 from shoulder 83 to face 85 of the cap 78.

Figure 22:
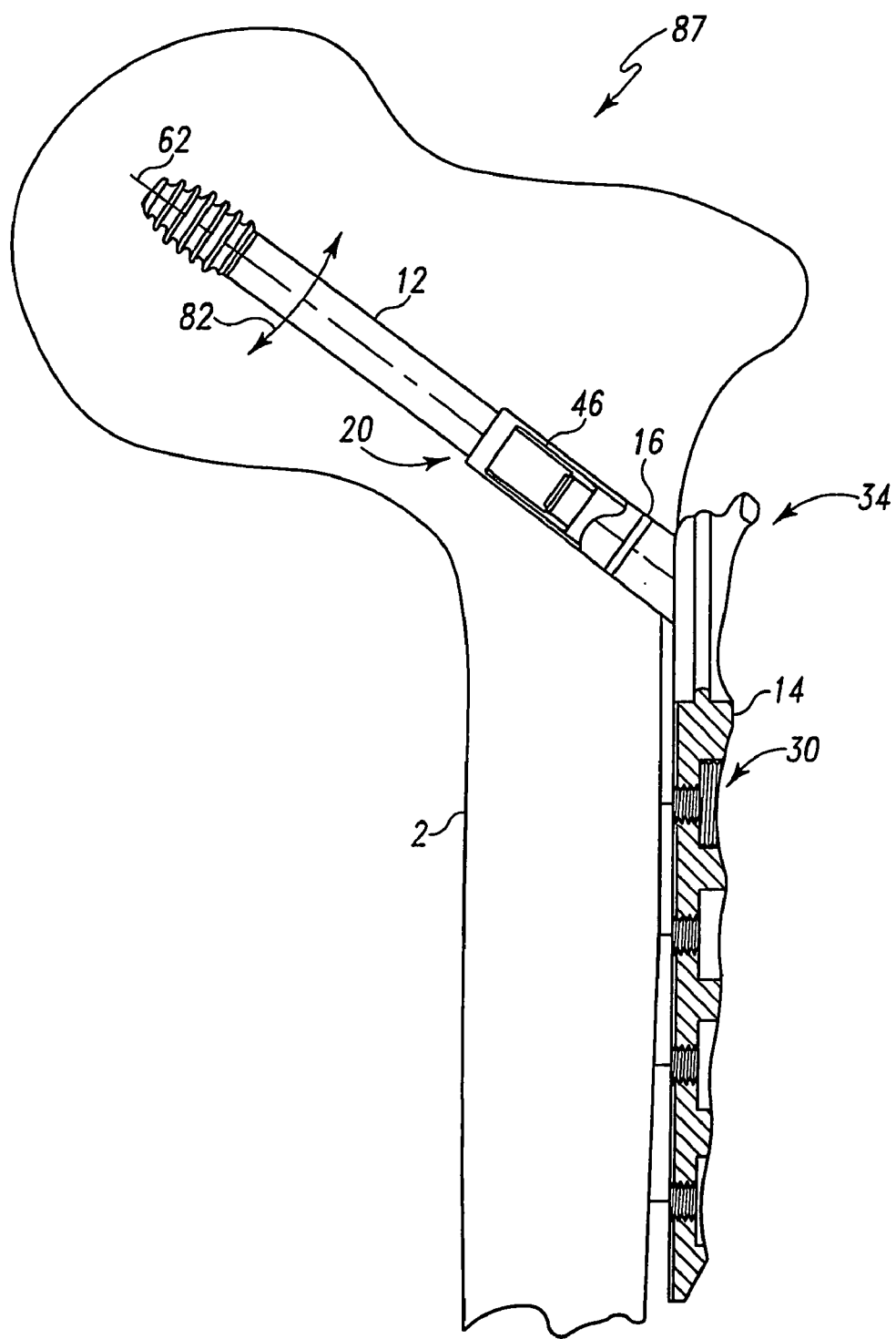
FIG. 22 is a plan view, partially in cross section, of a hip screw assembly according to another embodiment of the present invention without the key and key screw.
Figure 23:
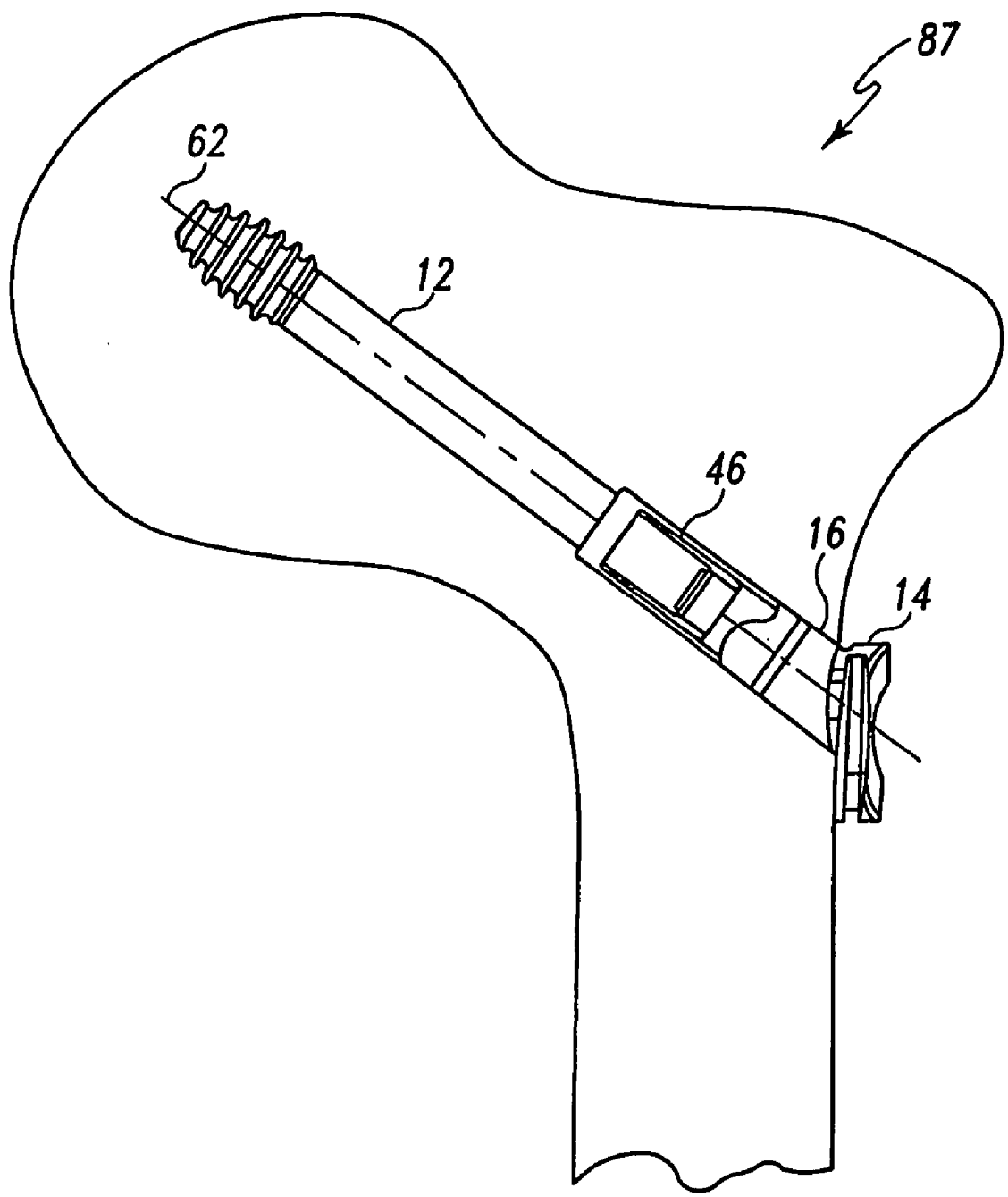
FIG. 23 is a plan view, partially in cross section, of the screw and barrel of the hip screw assembly of FIG. 22.

Referring now to FIGS. 22 and 23, another embodiment of the present invention is shown as hip screw assembly 87. Hip screw assembly 87 is similar to the hip screw assembly 10 of FIGS. 1 through 21 and includes some of the same components of as the hip screw assembly 10. The hip screw assembly 87, however, does not include the key 92 or the key screw 98. The hip screw assembly 87 further does not include first cap 58 or the second cap 78.

As shown in FIGS. 22 and 23 the hip screw assembly 87 includes plate 14 which is secured to the femur 2 by screws 32. The barrel 16 is secured to plate 14. Sleeve 46 is fitted into barrel 16. The screw 12 is slideably fitted into sleeve 46. It should be appreciated that the hip screw 87 provides for compression or movement of the screw 12 along longitudinal axis 62. The hip screw assembly 87 does not provide for anti-rotation and the screw 12 may rotate in the direction of arrows 82.

Referring now to FIGS. 24, 24A and 24B, yet another embodiment of the present invention is shown as hip screw assembly 110. The hip screw assembly 110 of FIGS. 24 and 24A is similar to the hip screw assembly 10 of FIGS. 1 through 21 except the hip screw assembly 110 does not include the compression limiting feature. The hip screw assembly 110 however does provide for the anti-rotation feature. The hip screw assembly 110 includes a screw 112 similar to the screw 12 of the hip screw assembly 10 except that the hip screw assembly 112 does not provide for an anti-rotation feature. The screw 112 receives sleeve 146.

The sleeve 146 includes a sleeve protrusion 190 similar to the sleeve protrusion 90 of the sleeve 46 of the hip screw assembly 10. The sleeve protrusion 190 matingly fits with barrel groove 188 formed in barrel 116. The barrel 116 is similar to the barrel 16 of the hip screw assembly 10 and includes a flange 137 which is operatively connected to plate 114. The plate 114 is similar to the plate 14 of the hip screw assembly 10. The flange 137 of the barrel 116 is secured to the plate 114 by, for example, barrel plate connection 134. The hip screw assembly 110 includes a key 192 similar to the key 92 of the hip screw assembly 10.

The hip screw assembly 110 includes a key screw 198 similar to the key screw 98 of the hip screw assembly 10. The key 192 is secured to the screw 112 by the key screw 198. The key 192 includes flats which angularly orient the sleeve 146 with the screw 112. The sleeve 146 includes a first end 189 which is resisted by shoulder 170 of the barrel 116 in the direction of arrow 187. The sleeve 146 however is able to move uninhibited in the direction of opposed to the arrow 187.

Referring now to FIG. 24A the shoulder 170 of the barrel 116 is shown with the shoulder 170 in contact with end 189 of the sleeve 146.

Referring now to FIG. 24B yet another embodiment of the present invention is shown as hip screw assembly 110B. The hip screw assembly 110B includes a flange 137B which is threadably engaged with barrel 116B to provide a stop or a limit in the direction opposed to arrow 187B.

Referring now to FIGS. 25, 25A, 25B, 25C and 25D, yet another embodiment of the present invention is shown as hip screw assembly 210. The hip screw assembly 210 is similar to the hip screw assembly 10 of FIGS. 1 through 21, except that the hip screw assembly 210 does not include a anti-rotation feature, but includes a compression length adjustment feature.

The hip screw assembly 210 includes a screw 212 similar to the screw 12 of FIGS. 1 through 21, except that the screw 212 includes features to provide for anti-rotation. The screw 212 slideably fits in cavity 218 of barrel 216. The barrel 216 is similar to the barrel 16 of the hip screw assembly 10 of FIGS. 1 through 21, except that the barrel 216 does not include a feature to prevent rotation of the screw 212 in the barrel 216. The screw 212 includes internal threads 283 which mate with external threads 285 formed on end screw 281. The end screw 281 provides a stop for the screw 212 in the direction of arrow 287 by having the end screw 281 contact shoulder 279 formed on barrel 216. The screw 212 is limited in movement in the direction opposed to arrow 287 along longitudinal axis 262 by cap 258 which is threadably engaged with barrel 216. The barrel 216 is connected by connector 234 to plate 214. The plate 214 may be similar to the plate 14 of the hip screw assembly 10 of FIGS. 1 through 21.

Figure 25:
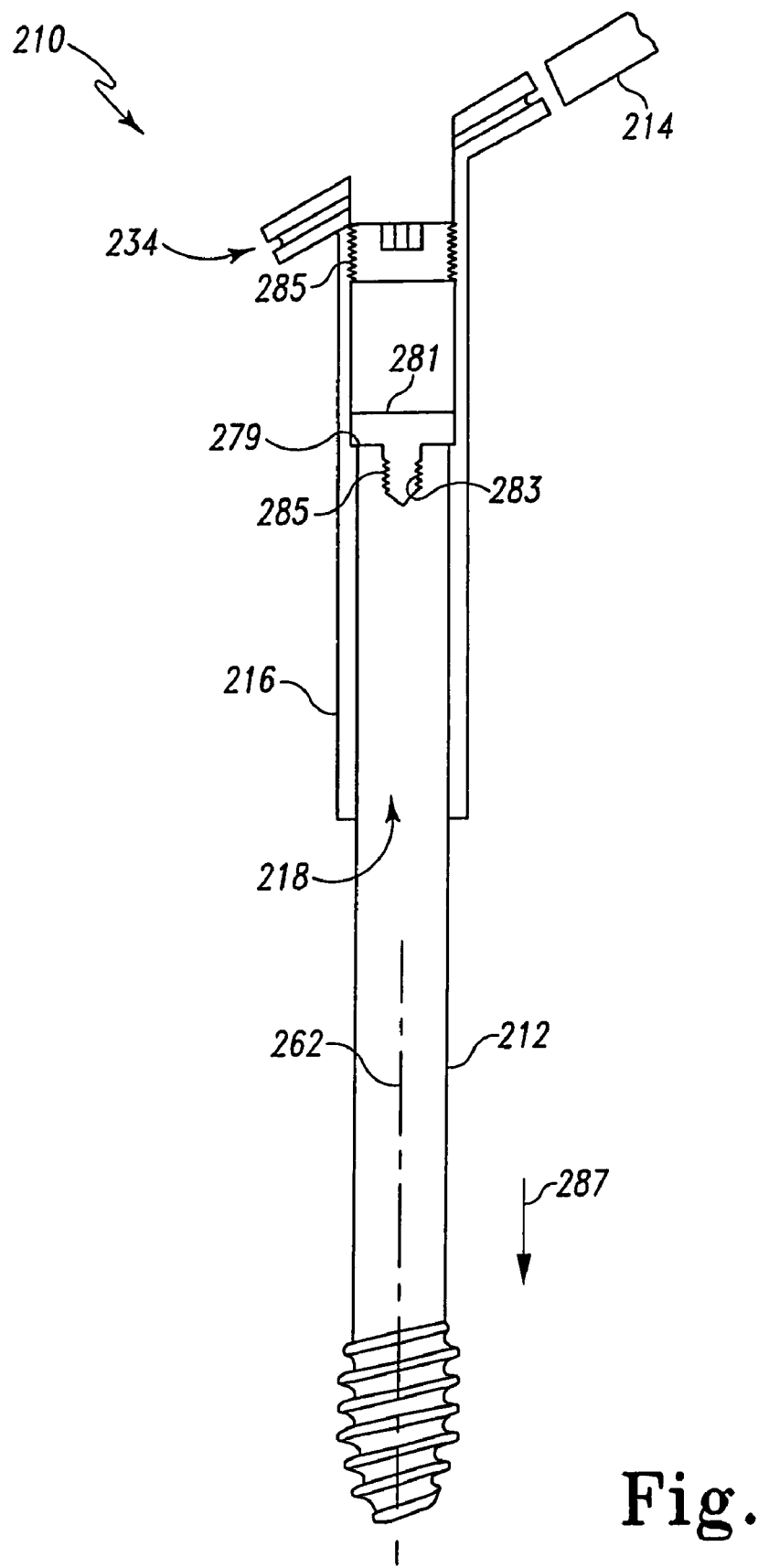
FIG. 25 is a plan view, partially in cross-section, of yet another embodiment of a hip screw assembly according to an embodiment of the present invention showing a screw with a selectable collapse length feature.
Figure 25A:
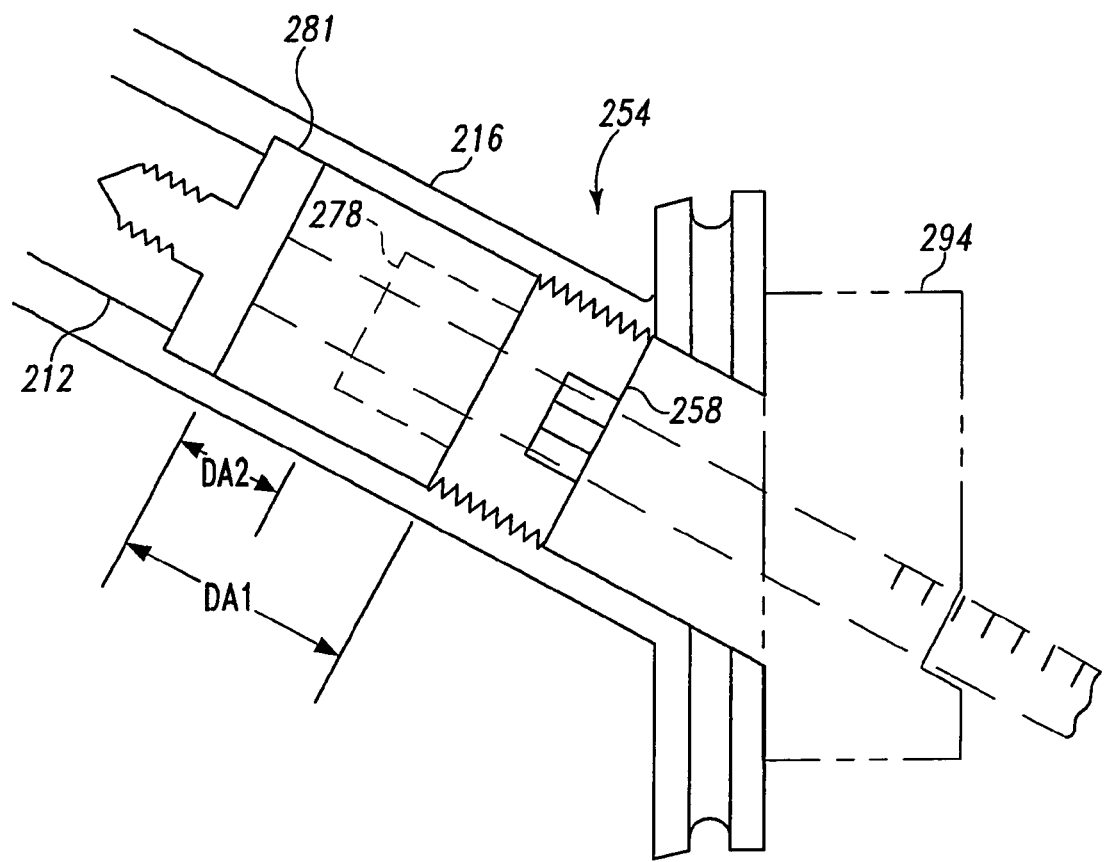
FIG. 25A is a partial plan view, partially in cross-section, showing a hip screw assembly with a plurality of different stops to provide a selectable collapse length feature according to yet another embodiment of the present invention.

Referring now to FIG. 25A, the hip screw assembly 210 is shown in first arrangement 254 as shown in solid with the cap 258 secured to barrel 216. The cap 258 and the barrel 216 provide for first arrangement 254 with first distance DA1. The distance DA1 represents the allowed axial movement of the screw 212 between end screw 281 and cap 258.

As shown in Phantom a second cap screw 278 provides for a distance DA2 between the end screw 281 and the cap 278. The cap 278 in use with the hip screw assembly 210 provides for second arrangement 256.

It should be appreciated that the surgeon may select the desired slide amount interoperatively using a measurement of the available slide distance AD1 after the lag screw 212 has been inserted into the femur. For example, a depth gauge 294 may be positioned laterally into the barrel 216 and the gage positioned against the end screw 281. A stop may then be selected from a variety of stops cap lengths from no slide to simply capping the end to prevent screw prominence or plate disengagement.

Figure 25B:
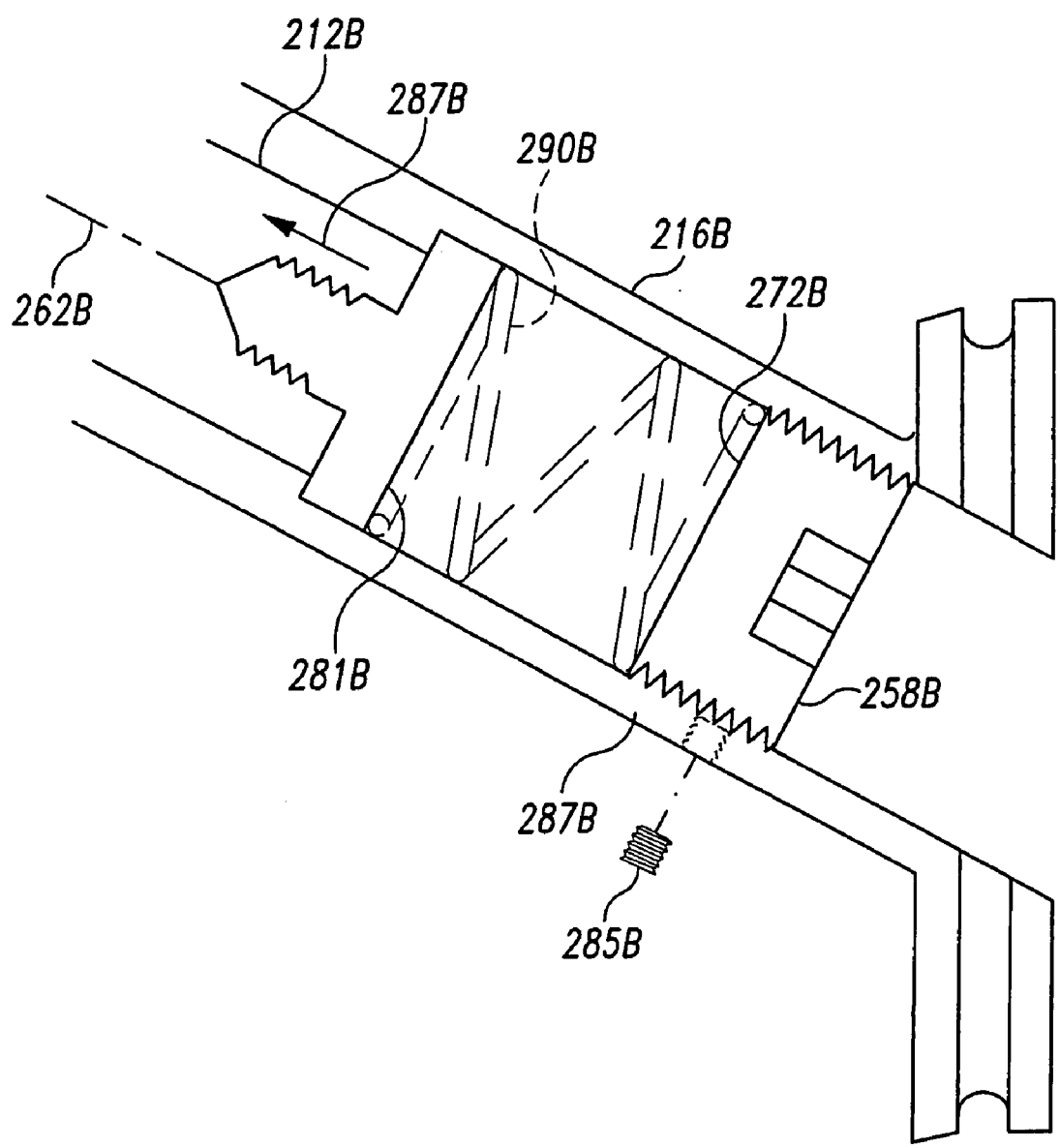
FIG. 25B is a partial plan view, partially in cross-section, showing a hip screw assembly with a threaded stop with a transverse set screw to provide a selectable collapse length feature according to another embodiment of the present invention.
Figure 25C:
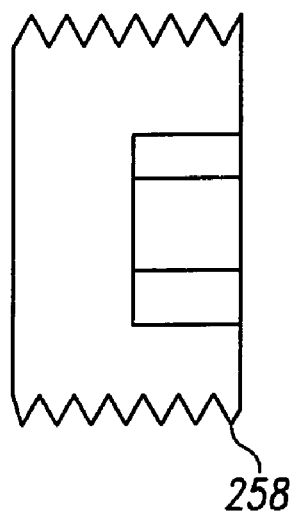
FIG. 25C is a cross sectional view of another alternate cap for use with the hip screw assembly of FIG. 25 according to another embodiment of the present invention.

Referring now to FIG. 25C the cap 258 is shown in greater detail.

Figure 25D:
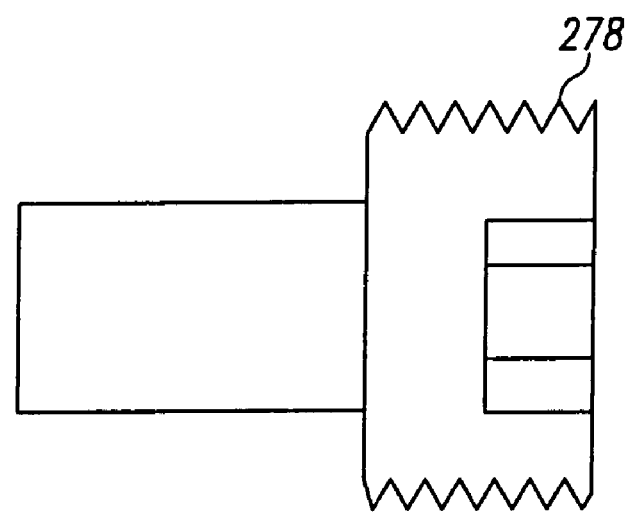
FIG. 25D is a cross sectional view of yet another alternate cap for use with the hip screw assembly of FIG. 25 according to another embodiment of the present invention.

Referring now to FIG. 25D cap 278 is shown in greater detail.

Referring now to FIG. 25B yet another embodiment of the present invention is shown as hip screw assembly 210B. The hip screw assembly 210B is similar to the hip screw assembly 210 except that rather than having a plurality of different length caps, the hip screw assembly 210B uses a single cap 258B which is threadably engaged with barrel 116B. Screw 212B slideably fits in barrel 218B. The screw 212B includes an end screw 281B which provides a stop for the screw 212B along longitudinal axis 262B in the direction of arrow 287B by having the end screw 281B mate against shoulder 270B of the barrel 216B.

Alternatively and as shown in FIG. 25B, the hip screw assembly of the present invention 25B (or any other of the embodiments described herein) may include the end screw 281B or the cap 258B that is in interference, yet permitted to slide within the barrel 216B such that the lag screw is permitted to collapse with resistance. In addition or in the alternative, a spring 290B may be positioned in the barrel 216B between the end screw 281B and the cap 258B to be used such that the lag screw is permitted to collapse with resistance.

The screw 212B may move from shoulder 270B to face 272B of the cap 258B. The cap 258B may, as it is threadably secured to the barrel 216, be advanced or retracted along longitudinal axis 262B by rotating the cap 258B. The cap 258B may be locked in any position by, for example, set screw 258B, which is threadably secured to threaded opening 287B of barrel 216B.

Figure 26:
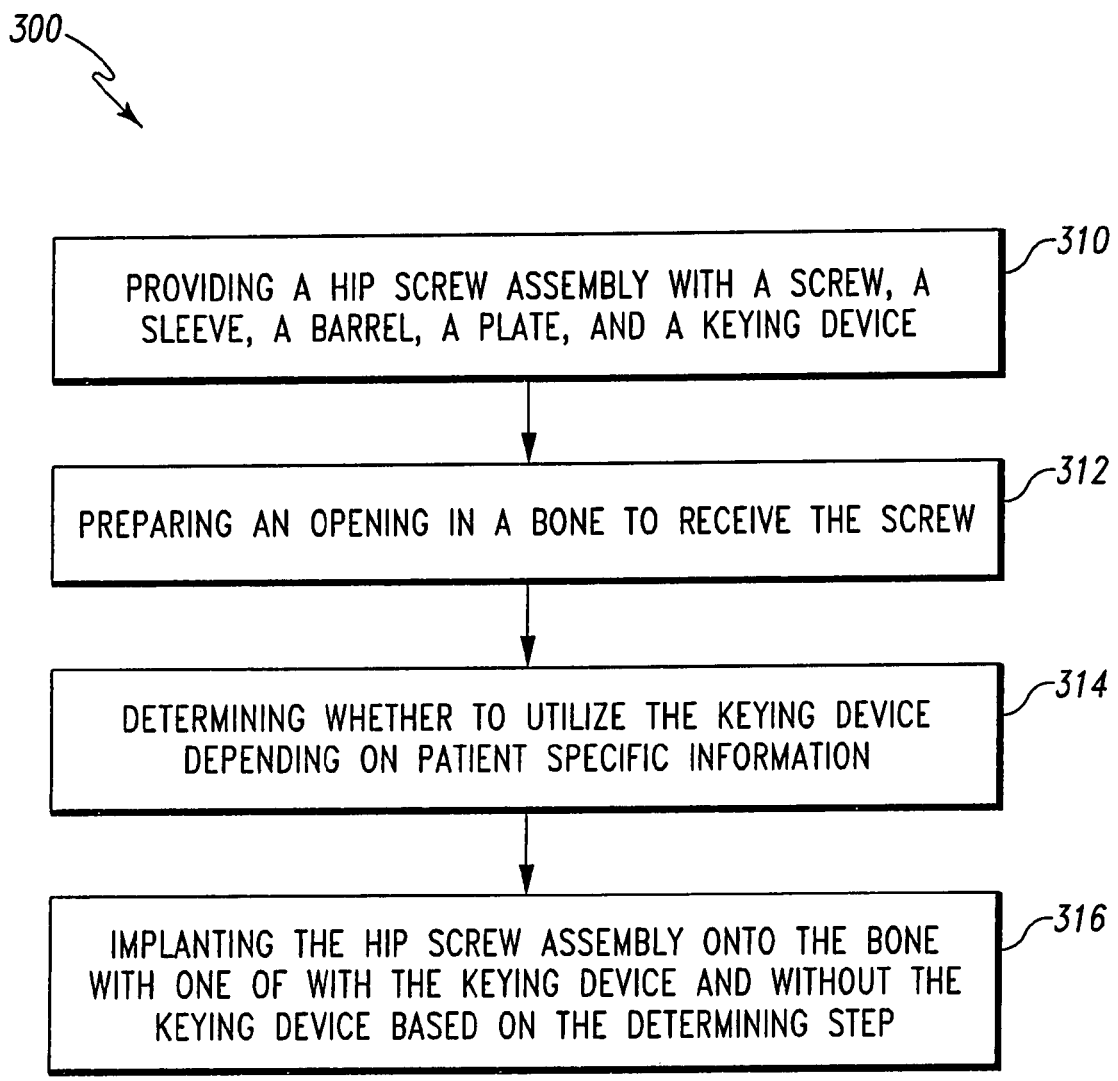
FIG. 26 is a flow chart of a surgical procedure according to another embodiment of the present invention.

Referring now to FIG. 26 yet another embodiment of the present invention is shown as surgical procedure 300. The surgical procedure 300 includes a step 310 of providing a hip screw assembly with a screw, a sleeve, a barrel, a plate, and a can device. The surgical procedure 300 also includes step 312 of preparing an opening in a bone to receive the screw. The surgical procedure 300 further includes a step 314 of determining whether to utilize the keying device depending on patients specific information. The method 300 further includes step 316 of the implanting the hip screw assembly onto the bone with the keying device and without the keying device based upon the determining step.

Figure 27:
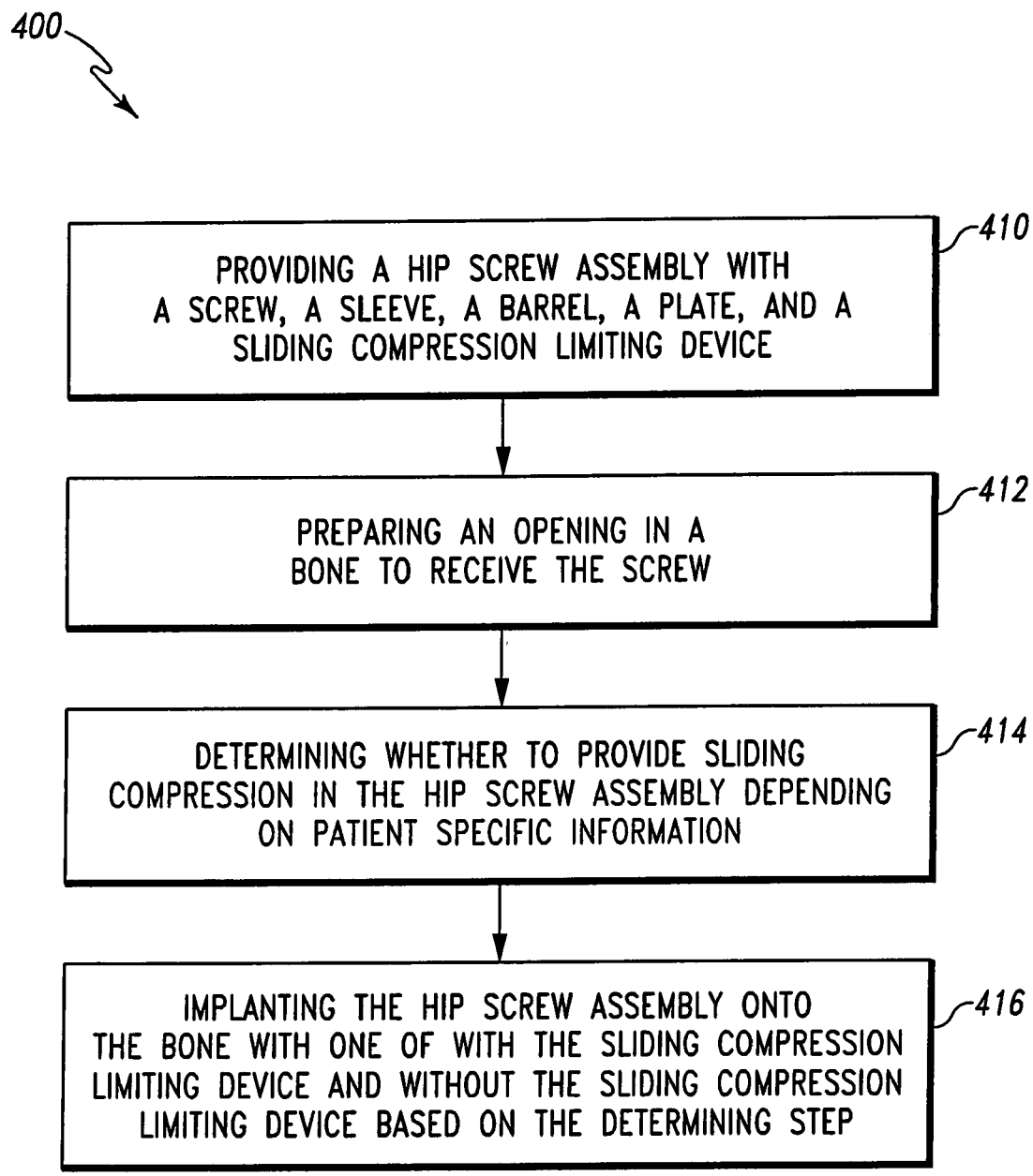
FIG. 27 is a flow chart of another surgical procedure according to another embodiment of the present invention.

Referring now to FIG. 27, yet another embodiment of the present invention is shown as surgical method or procedure 400. The method 400 includes step 410 of preparing a hip screw assembly with a screw, a sleeve, a barrel, a plate, and a sliding compression limiting device. The method 400 also includes step 412 of preparing an opening in a bone to receive the screw. The method 400 further includes 414 step of determining whether to provide sliding compression in the hip screw assembly depending on patients specific information. The method 400 further includes step 416 of implanting the hip screw assembly onto the bone with one of, with the sliding compression limiting device and without the sliding compression limiting device, based upon the determining step.

According to another aspect of the method 400 for performing trauma surgery, the providing a hip screw assembly step includes providing the sliding compression limiting device comprises providing the sliding compression limiting device with a plurality of compression length settings, the determining step includes determining the compression length setting desired if any sliding compression should be allowed with the hip screw assembly depending on patient specific information, and the implanting the hip screw assembly step includes implanting the hip screw assembly with the desired compression length setting if any sliding compression should be allowed based on the determining step.

According to another aspect of the method 400 for performing trauma surgery, the sliding compression limiting device provides lateral backout prevention, the determining step includes determining whether lateral backout should be prevented with the hip screw assembly depending on patient specific information, and the implanting the hip screw assembly step includes implanting the hip screw assembly with the sliding compression limiting device if any lateral backout should be prevented based on the determining step.

According to another aspect of the method 400 for performing trauma surgery, the method also includes step of measuring the available sliding distance of the screw in the barrel after screw insertion and the step of providing a plurality of stops. The stops have one of a plurality of lengths and are positionable in the barrel. The implanting the hip screw assembly step includes implanting the hip screw assembly with a selected one of the plurality of stops to provide a sliding distance for the hips screw assembly based on the measured available sliding distance of the screw in the barrel.

Although the present invention and its advantages have been described in detail, it should be understood that various changes, substitutions, and alterations can be made therein without departing from the spirit and scope of the present invention as defined by the appended claims.

We claim:

1. A hip screw assembly kit for fixation of a fractured femur, the screw assembly kit comprising:
    a screw for engagement with the femur;
    a plate for engagement with the femur;
    a barrel defining a cavity therein, said barrel secured to said plate and defining a first stop, said screw including a portion thereof fitted in the cavity of said barrel;
    a second stop positionable in said barrel, said second stop providing a limit on the movement of said screw when positioned in said barrel at a first distance away from the first stop, wherein said screw is slideably moveable in the cavity of said barrel along the first distance;
    and a third stop positionable in said barrel, said third stop providing a limit on the movement of said screw when positioned in said barrel at a second distance away from the first stop, wherein said screw is slideably moveable in the cavity of said barrel along the second distance, wherein the second distance is greater than the first distance;
    and a sleeve positioned between said barrel and said screw.

2. The hip screw assembly kit of claim 1, wherein said second stop is threadably engagable with said barrel.

3. The hip screw assembly kit of claim 2, further comprising a set screw to lock said stop in a fixed position.

4. The hip screw assembly kit of claim 1, further comprising a key for angularly orienting said screw with respect to said sleeve.

5. The hip screw assembly kit of claim 4 wherein:
    said sleeve defines an angular orientation feature on said sleeve; and
    said barrel defines an angular orientation feature on said barrel, the angular orientation feature on said sleeve cooperates with the angular orientation feature on said barrel for angularly orienting said sleeve to said barrel.

6. The hip screw assembly kit of claim 5, wherein said key defines first and second spaced apart key flats, the first flat on said key cooperates with a first flat on said screw for angularly locking said key to said screw, the second flat on said key cooperating with a first flat on said sleeve for angularly locking said key to said sleeve.

7. A hip screw assembly for fixation of a fractured femur, the screw assembly comprising:
    a screw for engagement with the femur, said screw defining a screw longitudinal centerline thereof;
    a plate for engagement with the femur;
    a barrel defining a cavity therein, said barrel secured to said plate, said screw including a portion thereof fitted in the cavity of said barrel; and
    a sleeve rotatably mounted to the screw such that rotation of the sleeve with respect to the screw does not cause axial movement of the sleeve with respect to the screw, the sleeve angularly fixed and slidable within the barrel.

8. The hip screw assembly of claim 7, wherein said screw and said barrel define a first arrangement there between in which said screw is slideably moveable in the cavity of said barrel a first distance and a second arrangement there between in which said screw is slideably moveable in the cavity of said barrel a second distance, said second distance being greater than said first distance.

9. The hip screw assembly of claim 8, further comprising a stop positionable in said barrel, said stop providing a limit on the movement of said screw in said barrel.

10. The hip screw assembly of claim 8, wherein said hip screw assembly defines a first arrangement including a key for angularly orienting said screw with respect to said sleeve and second arrangement not including said key.

11. The hip screw assembly of claim 7, further comprising a key for angularly orienting said screw with respect to said barrel.

12. The hip screw assembly of claim 7:
   further comprising a key for angularly orienting said screw with respect to said sleeve;
   wherein said sleeve defines an angular orientation feature on said sleeve; and
   wherein said barrel defines an angular orientation feature on said barrel, the angular orientation feature on said sleeve cooperates with the angular orientation feature on said barrel for angularly orienting said sleeve to said barrel.

13. The hip screw assembly of claim 12, wherein said key defines first and second spaced apart key flats, the first flat on said key cooperates with a first flat on said screw for angularly locking said key to said screw, the second flat on said key cooperating with a first flat on said sleeve for angularly locking said key to said sleeve.

14. The hip screw assembly of claim 13, wherein the first and second spaced apart key flats comprises a polygon pattern of equally spaced flats.

15. The hip screw assembly of claim 14, wherein the first and second spaced apart key flats comprises a hexagonal pattern.

16. The hip screw assembly of claim 12, further comprising a fastener for securing the key to one of said sleeve and said screw.

17. The hip screw assembly of claim 16:
   wherein said fastener includes a fastener key interlock feature;
   wherein said key includes a key fastener interlock feature; and
   wherein the fastener key interlock feature of said fastener and the key fastener interlock feature of said key cooperate to interconnect said fastener to said key.

18. The hip screw assembly of claim 12, wherein said key is adapted for selectively angularly orienting said screw with respect to said barrel in one of a plurality of positions.

19. The hip screw assembly of claim 13:
   wherein the angular orientation feature on said sleeve comprises a longitudinal protrusion; and
   wherein the angular orientation feature on said barrel comprises a longitudinal groove.

20. A hip screw assembly kit for fixation of a fractured femur, the screw assembly comprising:
   a screw for engagement with the femur, said screw defining a screw longitudinal centerline thereof;
   a plate for engagement with the femur;
   a barrel defining a cavity therein, said barrel secured to said plate;
   a sleeve defining an opening therethrough, said sleeve positioned at least partially in the cavity of said barrel and rotatably secured to the screw; and
   a key for selectively angularly fixing said screw and said sleeve.

21. The hip screw assembly of claim 20, wherein said screw and said barrel define a first arrangement there between in which said screw is slideably moveable in the cavity of said barrel while angularly fixed within said barrel.

22. The hip screw assembly kit of claim 21, further comprising a first stop positionable in said barrel, said first stop providing a first limit on the slidable movement of said screw in said barrel.

23. The hip screw assembly kit of claim 22:
   further comprising a second stop positionable in said barrel, said second stop providing a second limit on the movement of said screw in said barrel, wherein the second limit is at a location different from a location of the first limit.

24. The hip screw assembly kit of claim 20:
   wherein said sleeve defines an angular orientation feature on said sleeve; and
   wherein said barrel defines an angular orientation feature on said barrel, the angular orientation feature on said sleeve cooperates with the angular orientation feature on said barrel for angularly orienting said sleeve to said barrel.

25. The hip screw assembly kit of claim 24:
   wherein the angular orientation feature on said sleeve comprises a longitudinal protrusion; and
   wherein the angular orientation feature on said barrel comprises a longitudinal groove.

26. The hip screw assembly kit claim 20, wherein said key defines first and second spaced apart key flats, the first flat on said key cooperates with a first flat on said screw for angularly locking said key to said screw, the second flat on said key cooperating with a first flat on said sleeve for angularly locking said key to said sleeve.

27. The hip screw assembly kit of claim 26, wherein the first and second spaced apart key flats comprises a polygon pattern of equally spaced flats.

28. The hip screw assembly kit of claim 27, wherein the first and second spaced apart key flats comprises a hexagonal pattern.

29. The hip screw assembly kit of claim 20, further comprising a fastener for securing the key to one said sleeve and said screw.

30. The hip screw assembly kit of claim 20, wherein said key is adapted for selectively angularly orienting said screw with respect to said barrel in one of a plurality of positions.

31. A method for performing trauma surgery comprising the steps of:
   providing a hip screw assembly with a screw, a sleeve rotatably mounted on the screw such that rotation of the sleeve with respect to the screw does not cause axial movement of the sleeve with respect to the screw, a barrel, a plate, and a keying device;
   preparing an opening in a bone to receive the screw;
   determining whether to utilize the keying device depending on patient specific information; and
   implanting the hip screw assembly onto the bone with the screw at least partially in the bone and with one of with the keying device and without the keying device based on the determining step.

32. A method for performing trauma surgery comprising the steps of:
   providing a hip screw assembly with a screw, a sleeve rotatably mounted on the screw such that rotation of the sleeve with respect to the screw does not cause axial movement of the sleeve with respect to the screw, a barrel, a plate, and a sliding compression limiting device;
   preparing an opening in a bone to receive the screw;
   determining whether to provide sliding compression in the hip screw assembly depending on patient specific information; and
   implanting the hip screw assembly onto the bone with the screw at least partially in the bone and with one of with the sliding compression limiting device and without the sliding compression limiting device based on the determining step.

33. The method of claim 32:
wherein the sliding compression limiting device provides lateral backout prevention;
wherein the determining step comprises determining whether lateral backout should be prevented with the hip screw assembly depending on patient specific information; and
wherein the implanting the hip screw assembly step comprises implanting the hip screw assembly with the sliding compression limiting device if any lateral backout should be prevented based on the determining step.

34. The method of claim 32:
further comprising the step of measuring the available sliding distance of the screw in the barrel after screw insertion;
further comprising the step of providing a plurality of stops, the stops having one of a plurality of lengths and positionable in the barrel; and
wherein the implanting the hip screw assembly step comprises implanting the hip screw assembly with a selected one of the plurality of stops to provide a sliding distance for the hips screw assembly based on the measured available sliding distance of the screw in the barrel.

35. The method of claim 32:
wherein the providing a hip screw assembly step comprises providing the sliding compression limiting device with a plurality of compression length settings;
wherein the determining step comprises determining the compression length setting desired if any sliding compression should be allowed with the hip screw assembly depending on patient specific information; and
wherein the implanting the hip screw assembly step comprises implanting the hip screw assembly with the desired compression length setting if any sliding compression should be allowed based on the determining step.

* * * * *